United States Patent [19]
Booth et al.

[11] Patent Number: 6,077,537
[45] Date of Patent: Jun. 20, 2000

[54] NON-SEDATING ACRIVASTINE PRODUCT

[75] Inventors: Anthony Booth, Chester, N.J.; Harvey Dickstein, Cohassett, Mass.; Jeffrey R. Koup, Ann Arbor, Mich.

[73] Assignee: Warner-Lambert Company, Morris Plains, N.J.

[21] Appl. No.: 09/082,803

[22] Filed: May 21, 1998

Related U.S. Application Data

[60] Provisional application No. 60/051,012, May 21, 1997.

[51] Int. Cl.$^7$ .............................. A61K 9/22; A61K 9/52
[52] U.S. Cl. ...................... 424/468; 424/457; 514/290; 514/778
[58] Field of Search .................................... 424/451, 457, 424/464, 468, 458, 469, 470, 484, 488; 514/290

[56] References Cited

U.S. PATENT DOCUMENTS

| | | | |
|---|---|---|---|
| 4,783,465 | 11/1988 | Sunshine et al. | 514/255 |
| 4,829,064 | 5/1989 | Sunshine et al. | 514/255 |
| 4,871,733 | 10/1989 | Sunshine et al. | 514/212 |
| 4,954,350 | 9/1990 | Jones et al. | 424/493 |
| 4,975,426 | 12/1990 | Sunshine et al. | 514/159 |
| 5,370,880 | 12/1994 | Jones et al. | 424/493 |
| 5,451,409 | 9/1995 | Rencher et al. | 424/468 |
| 5,456,921 | 10/1995 | Mateescu et al. | 424/465 |
| 5,603,956 | 2/1997 | Mateescu et al. | 424/488 |
| 5,616,343 | 4/1997 | Cartilier et al. | 424/464 |
| 5,645,858 | 7/1997 | Kotwal et al. | 424/495 |

FOREIGN PATENT DOCUMENTS

| | | |
|---|---|---|
| 0284408 | 9/1988 | European Pat. Off. . |
| 8808302 | 11/1988 | WIPO . |
| 9402121 | 2/1994 | WIPO . |

OTHER PUBLICATIONS

Pharmacokinetics of Acrivastine, A new $H_1$–Antagonist, Following Ascending Doses. N. S. Jallad, D. C. Garg, R. J. Fleck, S. H. Poe, M. R. Blum, J.W.A. Findlay, S.H.T. Liao, M. F. Frosolono, and D. J. Weidler, J. Clin. Pharaceutical; 985,25:632 (abstract), 1985.

Acrivastine. A Review of its Pharmacological Properties and Therapeutic Efficacy in Allergic Rhinitis, Urticaria and Related Disorders. Rex N. Brogden and Donna McTavish. Drugs 41 (6) 1991:pp. 927–540.

Pharmacodynamic and Pharmacokinetics of BW 825C: A New Antihistamine. A. F. Cohen, M. J. Hamilton, S. H. T. Liao, J.W. A. Findlay, and A. W. Peck. Eur J. Clin. Pharmacol (1985) 28: p. 197–204.

Pharmacokinetics of Acrivastine after Oral and Colonic Administration. Ramadas Balasubramanian, Kenneth B. Klein, A. Wayne Pittman, Sam H. T. Liao, John W. A. Findlay, and M. F. Frosolono J. Clin. Pharmacol (1989). 29: p. 444–447.

Development and application of a pharmacokinetics simulation program for oral controlled release dosage forms—DIPS. H. P. Jones, R. Clements, D. J. Hearn, M. J. Gamlen. International Journal of Pharmaceutics 104 (1994): pp. 253–270.

*Primary Examiner*—James M. Spear
*Attorney, Agent, or Firm*—Evan J. Federman

[57] ABSTRACT

The present invention relates to methods of using and compositions containing acrivastine which provide antihistaminic therapeutic benefits while minimizing undesirable central nervous system side effects. According to the present invention, the plasma concentration-response curve for acrivastine's sedative side effects is steeper than that of the plasma concentration-response curve for its antihistamine activity. Accordingly, when the peak blood plasma level of acrivastine is maintained within the levels provided by the present invention composition, the central nervous side effects are minimized while the antihistaminic effects are optimized.

46 Claims, 21 Drawing Sheets

Acrivastine Plasma Concentration vs. Time

FIG-1  Acrivastine Plasma Concentration vs. Time

FIG-3 % Increase in Body Sway vs. log conc.

FIG-6  Observed Cp vs Predicted Cp values for Flare

FIG-7 Observed vs Predicted Flare Response

FIG-8  Observed vs. Predicted Cp values for PSV

FIG-9  Observed vs Predicted PSV Response

FIG-10  Observed vs. Predicted Cp for Sway Response

FIG-11 Observed vs Predicted Sway Response

FIG-13 Steady State Cp (Flare) Four Formulations

NON-SEDATING ACRIVASTINE PRODUCT

This application claims benefit of the filing date pf copending U.S. Provisional Application No. 60/051,012, filed May 21, 1997.

INTRODUCTION

The present invention relates to sustained release formulations and methods of using acrivastine which provide an antihistamine therapeutic effect while minimizing and/or eliminating undesirable central nervous system side effects, such as sedation. The present invention provides controlled release oral preparations of acrivastine that produce lower and more uniform plasma levels of acrivastine relative to known immediate release compositions, causing the central nervous system side effects of acrivastine to be lowered more than antihistamine effects.

BACKGROUND OF THE INVENTION

Acrivastine, [(E)-3-(6-[3-pyrrolidino-1-(4-tolyl)-prop-1E-enyl]-2-pyridyl)-acrylic acid] is an analog of triprolidine (ACTIDIL™) having the following chemical structure:

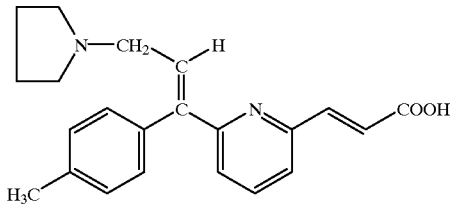

(Cohen et al., 1985, Eur. J. Clin. Pharmacol. 28:197–204;Brogden and McTavish, 1991, Drugs 41:927–940). The drug is an $H_1$-receptor antagonist which has a rapid onset of action but is rather short acting. This makes acrivastine particularly appropriate for "on demand" therapy of subjects suffering from intermittent symptoms of, for example, allergic rhinitis (Brogden and McTavish, 1991, Drugs 41:927–940). Acrivastine has low sedating potential—however, mild sedation is observed under laboratory conditions at dosages of 8 and 16 mg using the multiple sleep latency test (id.). Undesirable drowsiness has been observed after administration of 8 mg of acrivastine, but was less than that associated with a related compound, triprolidine (id., citing Hamilton et al., 1985, Br. J. Clin. Pharmacol. 19:585 P-586 P). Prior to the present invention, there had been no systematic evaluation of the relationship between acrivastine pharmacokinetics and antihistaminic or sedative responses (Jallard et al., 1985, J. Clin. Pharmacol. 25:629–637).

Thus, one undesirable side effect of acrivastine is mild sedation. Acrivastine is currently administered in the United States at doses of 8 mg, three times a day in combination with 60 mg pseudoephedrine as SEMPREX-D™ capsules, as described in the 1996 Physicians Desk Reference, p. 468. Acrivastine is rapidly absorbed from the combination capsule following oral administration and peak plasma levels are obtained between 1 to 2 hours post-ingestion. Acrivastine has been shown to follow linear pharmacokinetics at ascending doses from 2 mg to 32 mg t.i.d. (Jallad et al., 1985, J. Clin. Pharmacol. 25:632). Following single dose oral administration of acrivastine 4 mg capsules and 12 mg oral solution to healthy volunteers, mean peak plasma concentrations (Cmax) of 73 and 179 ng/mL were attained at 1.4 and 0.85 hours (Tmax), respectively (Sifton et al., 1996, Physician's Desk Reference, 50th edition, Montvale, N.J.). Mean apparent volume of distribution (Vd/F) has been reported as 0.64 and 0.75 L/Kg following single and multiple doses, respectively. Acrivastine binding to human plasma proteins, primarily albumin, was 50±2.0% and was concentration-independent over the range of 5 to 1000 ng/ml. The elimination half-life of acrivastine has been reported to be 1.7 hr, making it necessary to dose conventional, immediate-release formulations of acrivastine up to four times a day. Studies have shown that acrivastine is primarily eliminated by the kidneys. The principal active metabolite, a propionic acid analogue of acrivastine, is detected in plasma at concentrations well below those of parent compound (Brogden and McTavish, 1991, Drugs 6:927–940). Poor colonic absorption of acrivastine has led Balasubramanian et al. (1989, J. Clin. Pharmacol. 29:444–447) to suggest that development of sustained release formulations of acrivastine could be problematic.

SUMMARY OF THE INVENTION

The present invention is directed to a method of optimizing a first physiological effect of a pharmaceutical compound over a second physiological effect, by administering the pharmaceutical compound to a mammal in a controlled release formulation. The pharmaceutical compound is known to produce at least two physiological effects when the compound is administered in a composition that provides immediate release at a known dosage frequency. The inventors have discovered that when the pharmaceutical compound is administered in a controlled release formulation, which provides a lower peak plasma concentration and a more uniform plasma concentration than does an immediate release formulation of the same dosage, it is possible to optimize the first, desirable, physiological effect over another, undesirable, physiological effect. In one embodiment, the pharmaceutical compound is acrivastine, and the first, desirable, physiological effect is an antihistamine effect while the second, undesirable, physiological effect is sedation.

In the pharmaceutical industry, there are many technologies that are used to sustain or extend the time duration of a drug. These sustained release technologies reduce the number of times a drug has to be administered. Such technologies allow a larger dose of drug to be administered to extend the time duration of the therapeutic effect without initially driving the drug concentration in the blood to undesired levels. These sustained release technologies suppress any initial pharmacokinetic (pK) "spike" (or dose dumping) and maintain therapeutically desired levels of drug in the blood over extended periods of time, thereby allowing the drug to be dosed less frequently. Such technologies are often used to produce marketed "once-a-day" drug products.

In another embodiment, the invention is directed to a method of changing the pK profile of an immediate release drug product by using sustained release technology, but without changing the amount or drug administered or the dosing schedule of the drug in its immediate release formulation. Such changes could be desirable for two reasons. First, changing the pK profile to a therapeutically more desirable profile should produce a better product. For example, the drug would produce equal or improved efficacy without concomitant side-effects. Second, where there is a product already approved by governmental (FDA) regulation, regulatory approval of any new drug product based on the invention should be expedited due to the drug being administered in the same amounts and with the same frequency as the existing approved product.

The invention is directed to a method of administering a pharmaceutical compound, which has a known dosage schedule for mammals when used in an immediate release formula, by using the same dosage schedule but with a controlled release formula.

The known dosage schedule of a pharmaceutical compound using immediate release technology produces a known pK with a known AUC when administered to a mammal. The pK profile is the blood plasma concentration of the pharmaceutical compound over time. AUC is the area under the curve of the pK profile, which is a measure of the amount and time duration of drug in the blood and therefore a measure of the amount of therapeutic effect of the drug.

Many immediate release formulas produce a pK with a sharp initial peak that gradually tails off. The inventors have discovered that it is possible to minimize the peak in the pK profile, which can lead to adverse side effects, yet produce about the same AUC, therefore producing about the same beneficial therapeutic effect which reducing adverse side effects. This is achieved by administering the drug in the same dosage amount, that is the same amount of drug in each dose and the same number of doses, but using sustained release technologies.

More specifically the present invention relates to methods of using acrivastine which provide antihistaminic therapeutic benefits while minimizing and/or eliminating undesirable central nervous system side effects. According to the present invention, the plasma concentration-response curve for acrivastine's sedative side effects is steeper than that of the plasma concentration-response curve for its antihistamine activity. Thus, administration of formulations of the present invention, which provide lower peak plasma concentration but a more uniform plasma concentration, or bioavailability, than currently available acrivastine compositions, result in disproportionate lowering of the undesirable side effects, including central nervous system side effects, compared to the desired antihistamine effect.

The present invention also relates to the use of controlled release oral preparations of acrivastine that deliver a lower and more uniform blood plasma level of acrivastine, relative to known compositions, such that central nervous system side effects of acrivastine are disproportionately lowered more than antihistaminic effects. The controlled release oral preparations deliver a peak plasma concentration which is no more than about 70% of the peak acrivastine plasma concentration achieved by an immediate release formulation of the same dosage. Preferably, the present controlled release formulations of acrivastine provide a peak acrivastine plasma concentration of less than 100 ng/ml, and deliver a more uniform acrivastine plasma concentration throughout the dosing interval of about 20 ng/ml to about 90 ng/ml. The more uniform plasma concentration is more preferably about 40 to about 80 ng/ml. In particular, nonlimiting, embodiments of the invention, the present controlled release compositions achieve a peak plasma concentration within about one hour of administration. Plasma concentration of acrivastine means the amount of acrivastine and its metabolites in the plasma when measured by nonspecific radio immunoassay. In other nonlimiting embodiments of the invention, the present controlled release formulations are administered at the same dosing frequency as an immediate release acrivastine formulation of the same dosage.

In further nonlimiting embodiments of the invention, the controlled release acrivastine compositions achieve a peak plasma concentration of acrivastine such that, relative to the effects of the peak plasma concentration (140 ng/ml) achieved after administration of 8 mg immediate release acrivastine, the antihistaminic response, is decreased no more than about 10 to about 60 percent, and the neurological side effect is decreased by about 20 to about 88 percent.

DETAILED DESCRIPTION OF THE INVENTION

Figure 1:
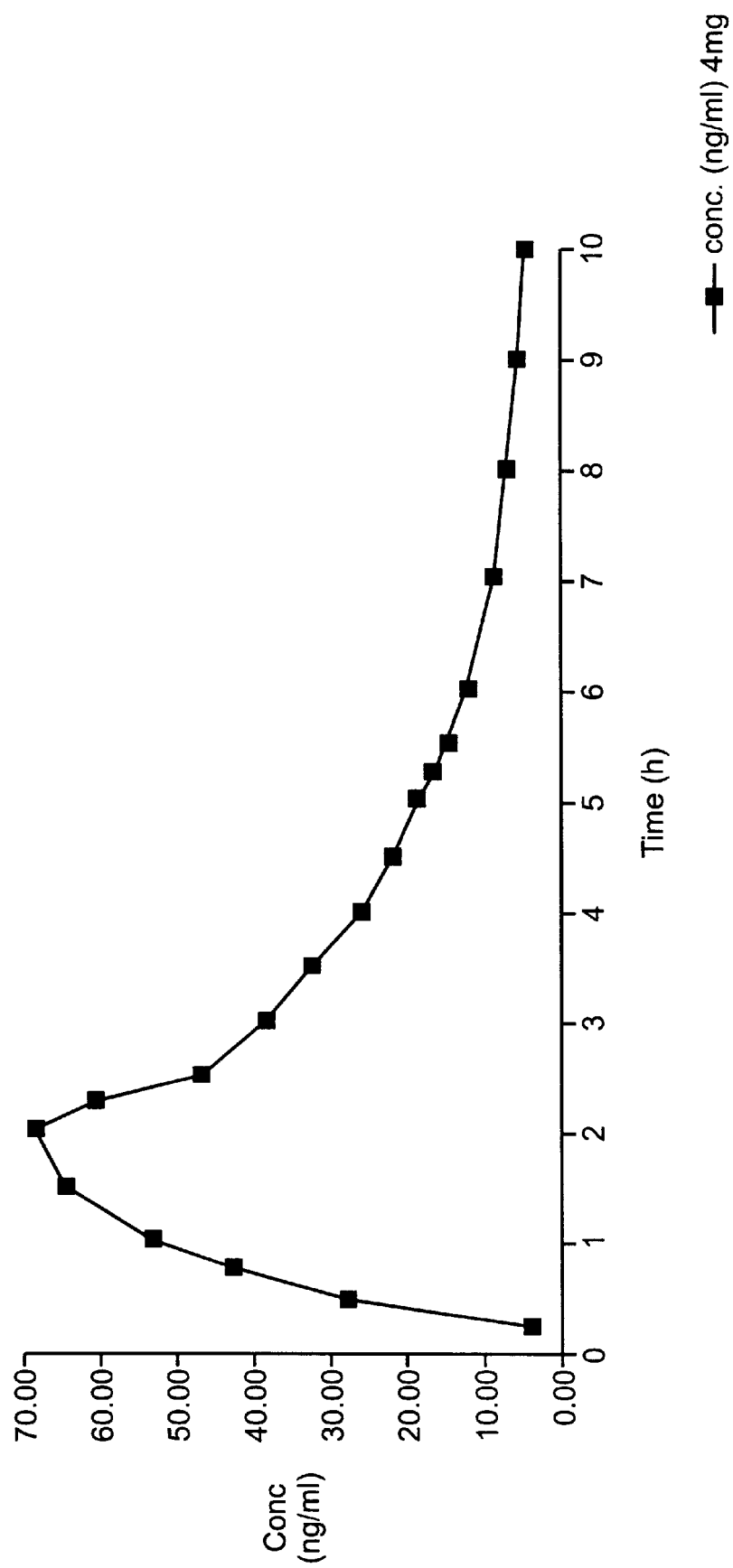
FIG. 1 Mean plasma concentration of acrivastine (n=12) following administration of a 4 mg oral acrivastine capsule.

The present invention relates to compositions containing, and methods of using, acrivastine which provide an antihistaminic therapeutic effect while minimizing and/or eliminating undesirable central nervous system side effects, such as sedation. According to the present inventions, as the plasma concentration of acrivastine is increased, the antihistaminic therapeutic effect tends to increase less acutely compared with the central nervous system side effects. Thus, for example, if peak blood plasma levels of acrivastine are lowered and made more uniform, the undesirable central nervous system side effects are disproportionately lowered more than the antihistaminic effects, while the beneficial antihistaminic effects are optimally sustained throughout the dosing interval.

The present invention provides compositions and methods for producing an antihistamine therapeutic effect comprising administering acrivastine at doses and intervals which produce a peak plasma concentration no more than about 70% of the peak acrivastine plasma concentration provided by an acrivastine immediate release formulation of the same dosage. Preferably, the peak acrivastine plasma concentrations provided by the present methods and formulations is less than about 100 ng/ml. Moreover, the present methods and formulations provide a more uniform acrivastine plasma concentration compared to immediate release acrivastine formulations of the same dosage. Preferably the more uniform acrivastine plasma concentrations achieved by the present invention are between about 20 ng/ml to about 90 ng/ml, and more preferably about 40 to about 80 ng/ml.

In particular, nonlimiting, embodiments of the invention, the peak plasma concentration is achieved within one hour of administration of acrivastine. Such a peak plasma concentration is no more than about 70% of the peak acrivastine plasma concentration provided by an immediate release formulation of the same dosage. Preferably, the present methods and formulations provide a peak acrivastine formulation of less than about 100 ng/ml. The acrivastine plasma concentration is preferably maintained between about 20 to about 90 ng/ml, and more preferably between about 40 to about 80 ng/ml.

In further nonlimiting embodiments of the invention, the peak plasma concentration of acrivastine may be such that, relative to the effects of the peak plasma concentration achieved after administration of 8 mg immediate release acrivastine, the antihistaminic response, as measured by inhibition of weal and flare following intradermal histamine injection, is decreased no more than about 8 to about 28 percent, while the neurological side effect, as measured by peak saccade velocity or body sway, is decreased by about 18 to about 55 percent. (See Example I).

In various embodiments of the invention, acrivastine may be administered orally in the form of a tablet, capsule, liquid, lozenge, etc. employing controlled release technology to achieve the above mentioned plasma concentrations. The dosages in such formulations, in specific nonlimiting embodiments of the invention, will preferably be about 8 mg given three times daily.

The present invention also provides for oral preparations of acrivastine by using controlled release technology. According to the present invention, such a controlled release formulation provides a rate of in vivo release for acrivastine which maintains or controls the peak plasma level of acrivastine within the concentration ranges contemplated by this invention while at the same time providing bioavailability equivalent to conventional immediate release formulations. As used herein bioavailability is the extent to which said acrivastine is absorbed in vivo from the present controlled release formulations to become available in the plasma. Bioavailability thus relates to the area under the curve of plasma concentration of acrivastine in the plasma over time.

The plasma concentration of an immediate release acrivastine formulation, during the normal dosing interval of that formulation, may range from a peak of about 140 ng/ml to a trough of about 5 ng/ml or less. The present controlled release formulations provide a more uniform plasma concentration, for example, between about 20 ng/ml to about 90 ng/ml. More preferably the acrivastine plasma concentrations provided by the present invention range from about 40 ng/ml to about 80 ng/ml. Thus, large variations in peak to trough plasma concentrations of acrivastine are avoided by the present methods and formulations, thereby providing optimal beneficial antihistaminic effects while minimizing undesirable side effects.

In one embodiment, the present controlled release acrivastine formulations are administered on the same dosing schedule as immediate release acrivastine formulations, but result in an optimal acrivastine plasma concentration which remains more uniform than that provided by conventional immediate release formulations. Thus, these controlled release formulations may be administered every four to six hours, resulting in smaller fluctuations in the plasma concentration of acrivastine than similarly dosed immediate release formulations, and providing excellent antihistamine effects while relieving side effects such as drowsiness.

In another embodiment, the present invention provides methods and formulations capable of producing an antihistaminic therapeutic effect which include administering a formulation containing acrivastine that provides a peak acrivastine plasma concentration of less than about 100 ng/ml. However, in this embodiment, the formulation also provides an area under the curve of time versus plasma concentration which is substantially equivalent to the area under the curve of an immediate release acrivastine formulation of a similar dosage. Thus, the present method and compositions provide optimal plasma concentrations of acrivastine to provide an antihistamine effect while avoiding or reducing undesirable side effects Those of skill in the art can prepare a controlled release formulation which provides the acrivastine plasma levels contemplated by the present invention, particularly in light of the teachings of the present invention. Controlled release formulations have been described in the literature. Such formulations may comprise acrivastine incorporated into microspheres or microcapsules, enteric coatings, coated core particles, or incorporated into a carrier matrix which controls the release of acrivastine in order to achieve the goals of this invention.

For example, but not by way of limitation, acrivastine may be incorporated in a matrix comprising high molecular weight hydrophilic, cellulose polymers or cross-linked amylose to impart sustained or controlled release. The skilled artisan can utilize such polymers or cross-linked amylose to make a sustained release matrix, for example, by coating, agglomerating, granulating or admixing the drug particles with the polymer.

Typical hydrophilic cellulose polymers used for this purpose, including sodium carboxy methylcellulose, hydroxypropylcellulose, hydroxypropylmethylcellulose, and hydroxyethylcellulose, are readily available commercially.

In a preferred embodiment, the controlled release formulations of the present invention include a mixture of acrivastine and cross-linked amylose. For example, about one part of acrivastine can be mixed with about five to twelve parts cross-linked amylose, and the mixture can be tableted to form a controlled acrivastine tablet of the present invention. Preferably, about one part acrivastine can be mixed with about seven to ten parts cross-linked amylose. Excipients can be added, such as lactose, microcrystalline cellulose, hydroxypropylcellulose and the like. Pancreatine can also be added to facilitate disintegration of the tablet. Preservatives, for example, sodium benzoate may also be added. The use of such cross-linked amylose in controlled release formulations is further described in U.S. Pat. Nos. 5,456,921, 5,603,956 and 5,616,343.

Such sustained release formulations using sustained release technology are administered at dosages and intervals which result in controlled release of acrivastine and the plasma concentrations set forth above.

Other methods of controlled administration of acrivastine which result in the aforementioned plasma concentrations, but which are administered by other routes, such as intranasal, intramuscular, subcutaneous, intravenous, or intrarectally, are also within the scope of the present invention.

Acrivastine may be administered in controlled release in combination with one or more other pharmaceutically active compounds, in a suitable carrier. Examples of such pharmaceutically active compounds include, but are not limited to, antitussives such as dextromethorphan, dextromethorphan hydrobromide, noscapine, carbetapentane citrate, and chlophedianol hydrochloride; antihistamines, such as chlorpheniramine maleate, phenindamine tartrate, pyrilamine maleate, doxylamine succinate, phenyltoloxamine citrate, diphenhydramine hydrochloride, promethazine, and tripolidine; decongestants, such as phenylephrine hydrochloride, phenylpropanolamine hydrochloride, pseudoephedrine hydrochloride, ephedrine; nonsteroid anti-inflammatory drugs (NSAID), such as acetylsalicylic acid acetaminophen, indomethacin, acemethacin, sulindac, piroxicam, ibuprofen, naproxen, ketoprofen; various alkaloid painkillers, such as codeine phosphate, codeine sulfate, and morphine; antiulcer products including $H_1$-and $H_2$-antagonists as well as proton pump inhibitors; and stimulants such as caffeine or theophylline. However, according to the present invention, (+)-pseudoephedrine is not included in the present acrivastine formulations.

EXAMPLE I

Dose/response Relationships of Acrivastine Antihistamine and CNS Effects

Traditional assessment of drug response has been based on empirical dose response relationships. Due to the linear relationship between log-dose and response, changes in drug dose cause smaller fractional changes in response than the fractional change in dose. These traditional approaches have not been useful in predicting the impact of modification in the rate of drug delivery on response as a function of time after dosing. To accomplish this objective, a model which was capable of predicting drug plasma concentration as a function of time (pharmacokinetics), and linking these concentrations to drug response as a function of time (pharmacodynamics), was required. The following model achieved this objective. This model used human pharmacokinetic and pharmacodynamic data from the literature (Cohen, et al., European Journal of Clinical Pharmacology, 1985 28:197–204; Cohen et al., European Journal of Clinical Pharmacology, 1987 32:279–288; Balasubramanian et al., 1989, J. Clin. Pharmacol. 29:444–447; Jones et al., 1994, Int'l J. of Pharm. 104:253–270).

For example, pharmacokinetic data were obtained from a study in which twelve healthy volunteers were given a 4 mg oral acrivastine capsule and plasma concentrations were measured as a function of time. Cohen et al, 1985, supra; A replot of these concentration vs. time data is shown in FIG. 1. Each subject was given 1, 2 and 4 mg of acrivastine respectively in a cross-over designed study with four concentrations of histamine acid phosphate. Data obtained following the 0.4 μg histamine dose was used in the present model because the widest range of inhibition of flare response was observed at that dose.

Figure 2:
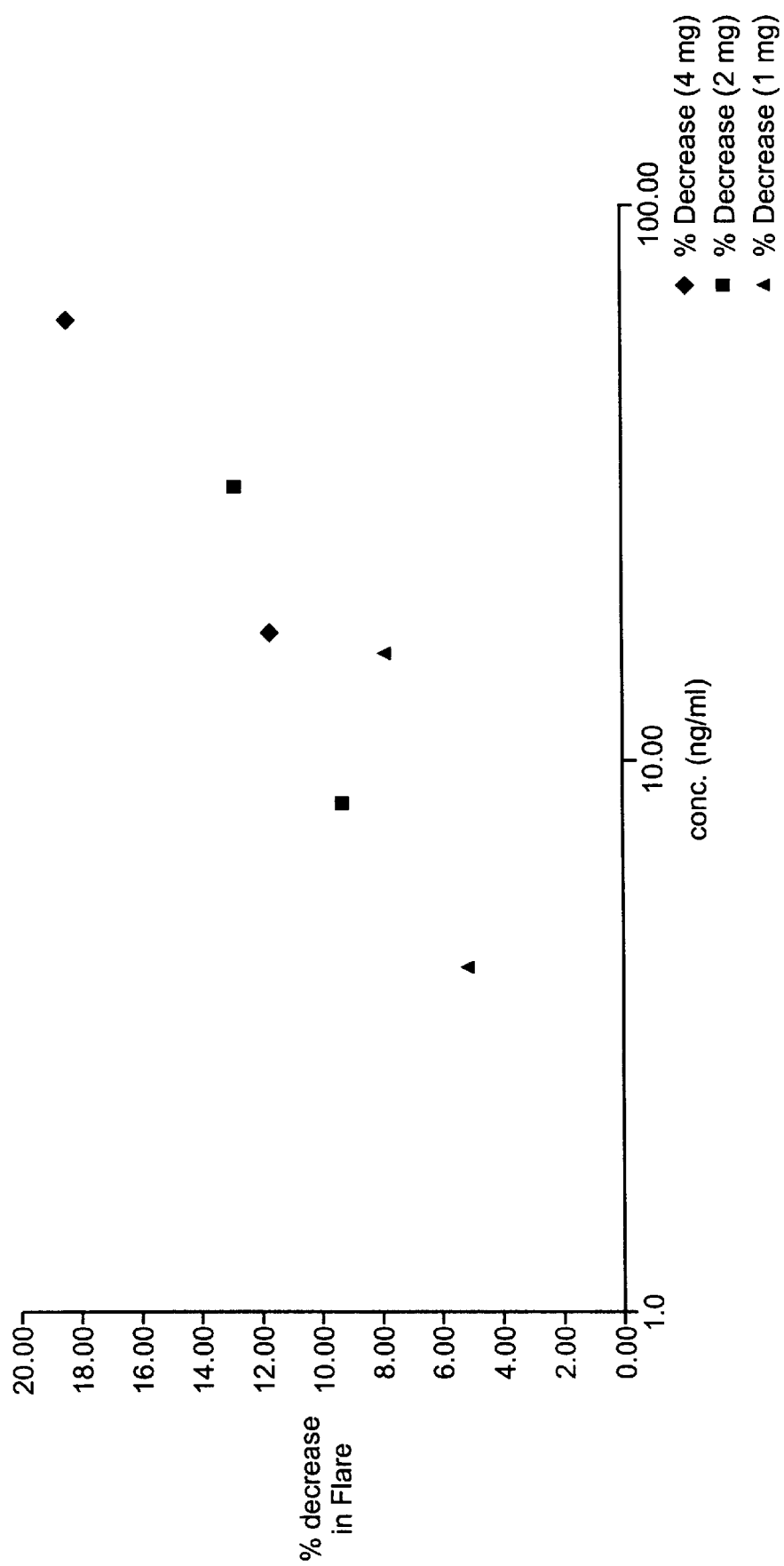
FIG. 2 Percent inhibition of flare response following intradermal injection of histamine versus log plasma concentration of acrivastine.

For assessment of the relationships between inhibition of flare response and plasma concentration at a 4 mg dose, plasma concentration values at 2.25 and 5.25 hours were selected from FIG. 1. Since the pharmacokinetics of acrivastine are linear, concentrations for the 2 and 1 mg doses were obtained by multiplying the concentrations observed following 4 mg by 0.5 and 0.25, respectively. The plot of inhibition of flare response related to acrivastine plasma concentration is shown in FIG. 2.

Two responses, body sway and peak saccade velocity (PSV) were used to characterize the sedative effects of acrivastine using the pharmacodynamic data (from Cohen et al., 1987, supra.). Identical gelatin capsules of acrivastine were used in the 1985 and 1987 studies by Cohen et al. indicating that the pharmacodynamics of the dosage form would be the same for the two studies. Average anteroposterior body sway was measured as degrees per minute using an ataxia meter. PSV, which is a measure of eye movement velocity, was recorded as degrees/second on a magnetic tape and analyzed by computer. Estimates for pharmacodynamic values for these two responses were obtained by inspection from the response vs time plots presented in the study. Plots of response vs drug plasma concentration were made by predicting concentrations at various time points as described above. These two relationships are presented in FIGS. 3 and 4.

Figure 3:
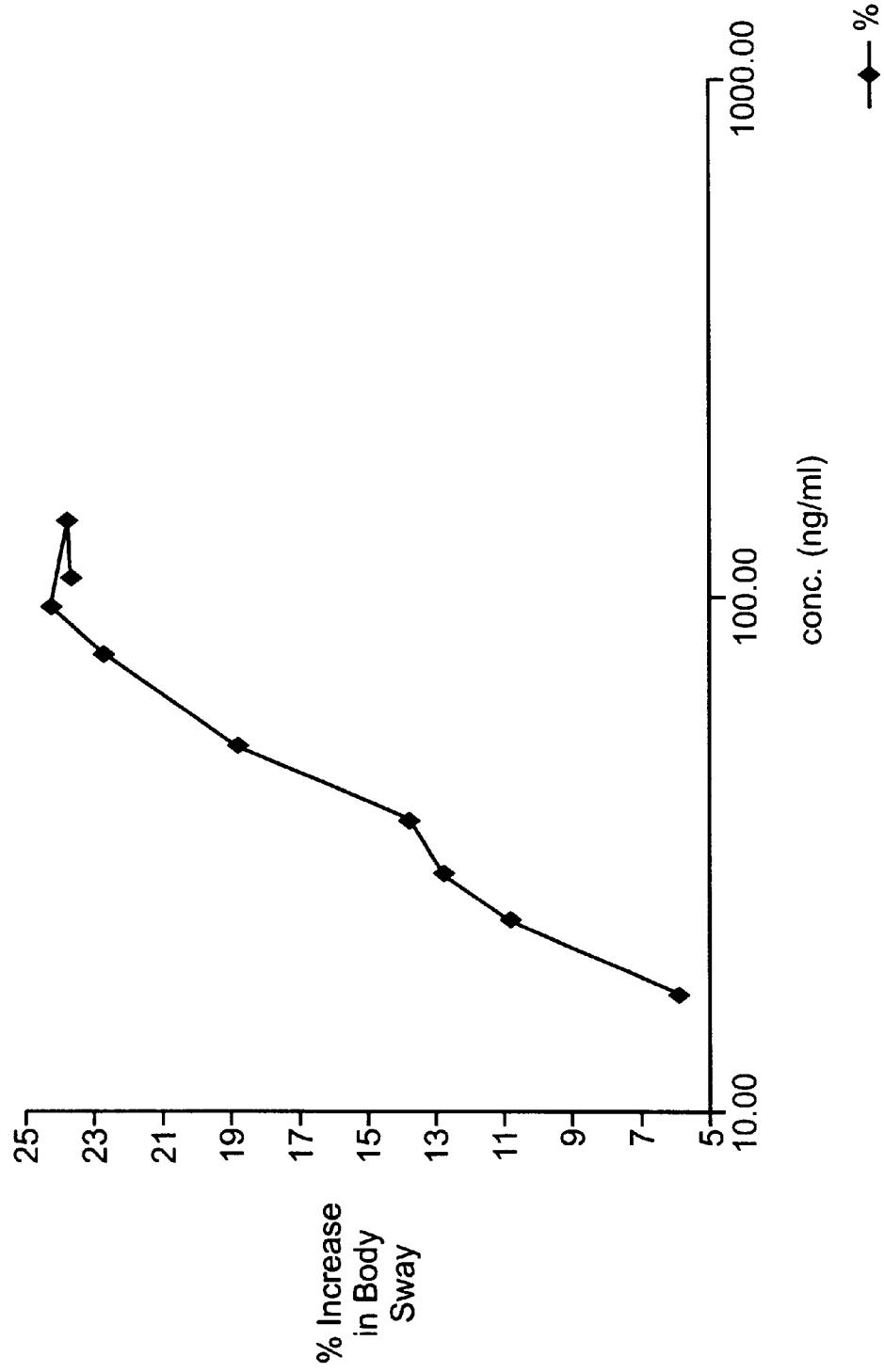
FIG. 3 Percent increase in body sway versus log concentration of acrivastine.
Figure 4:
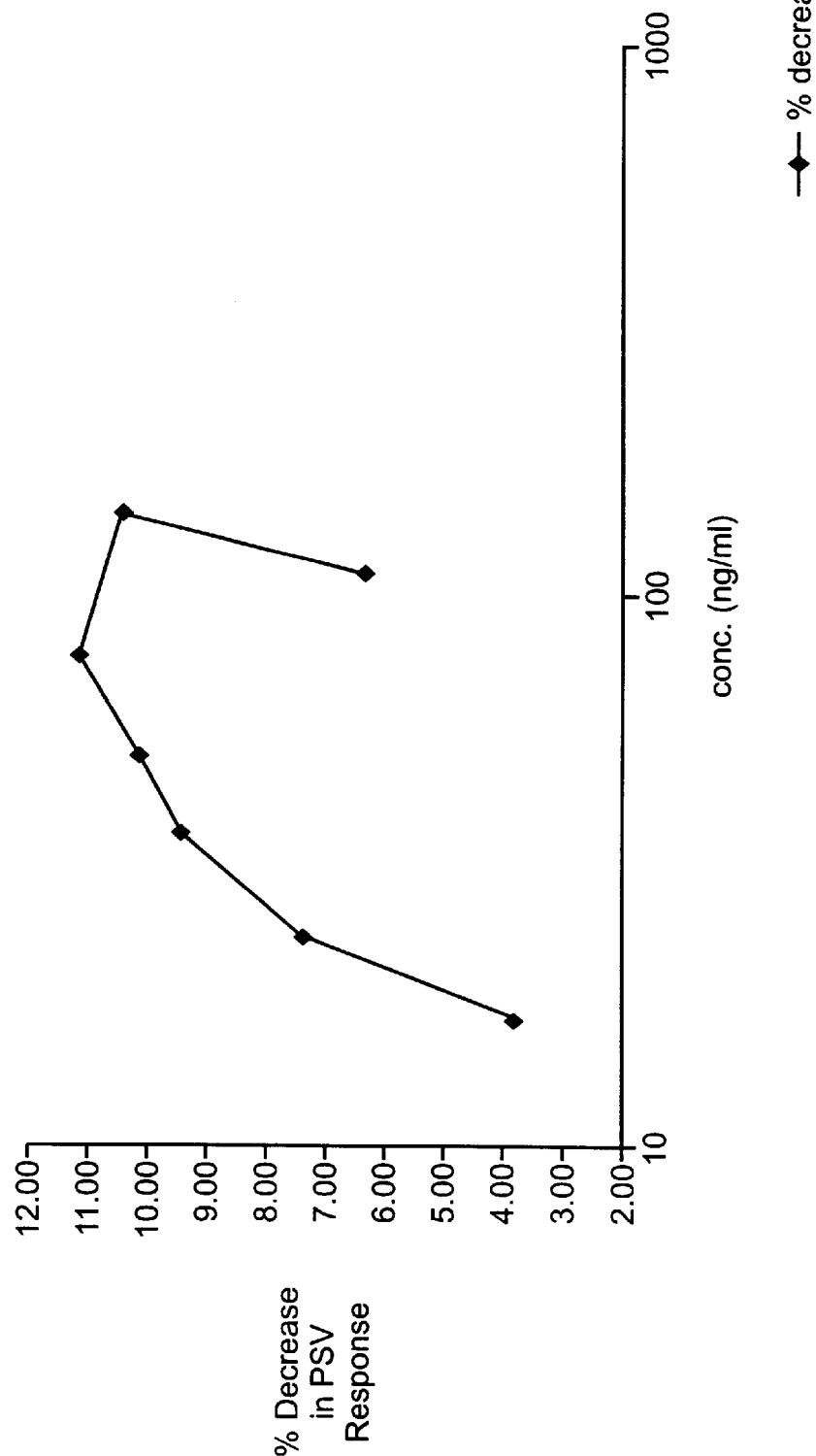
FIG. 4 Percent decrease in peak saccade velocity versus log concentration of acrivastine.

The plot for PSV vs. drug concentration in FIG. 4 demonstrated a counter-clockwise hysteresis loop indicating an equilibrium delay to the effect site. The plot for sway vs. drug concentration in FIG. 3 showed a fairly linear relationship indicating rapid distribution of acrivastine to the effect site where this particular response is elicited.

Figure 5:
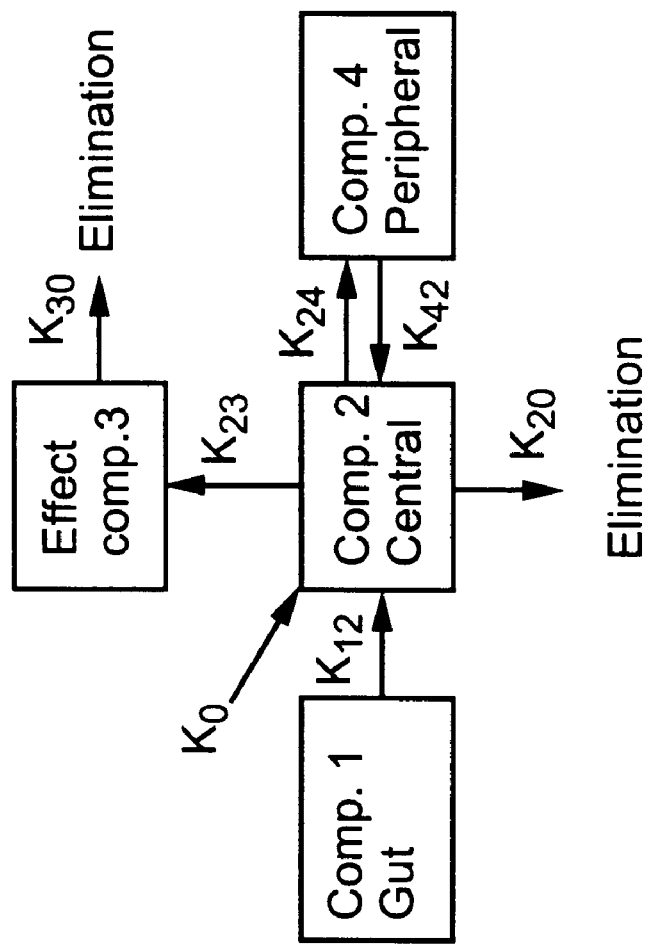
FIG. 5 Pharmacokinetic/pharmacodynamic model.
Figure 6:
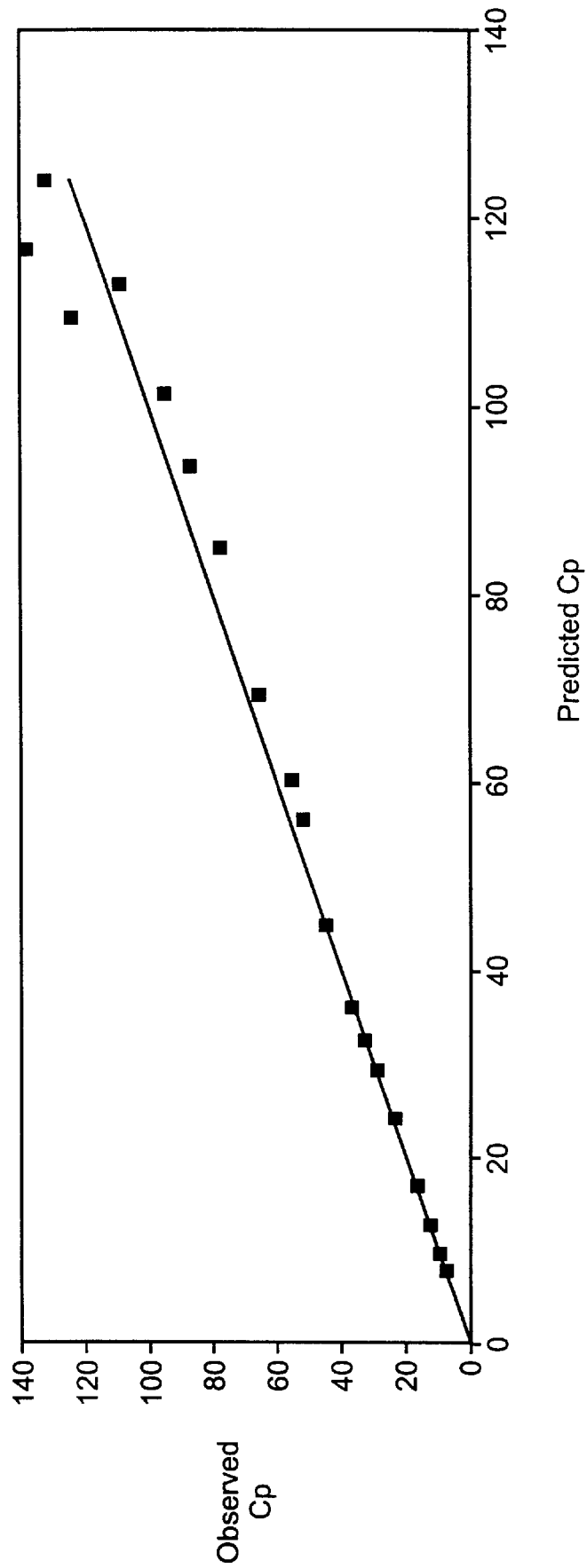
FIG. 6 Observed plasma concentration of acrivastine versus predicted plasma concentration based on model of FIG. 5, for flare response.
Figure 7:
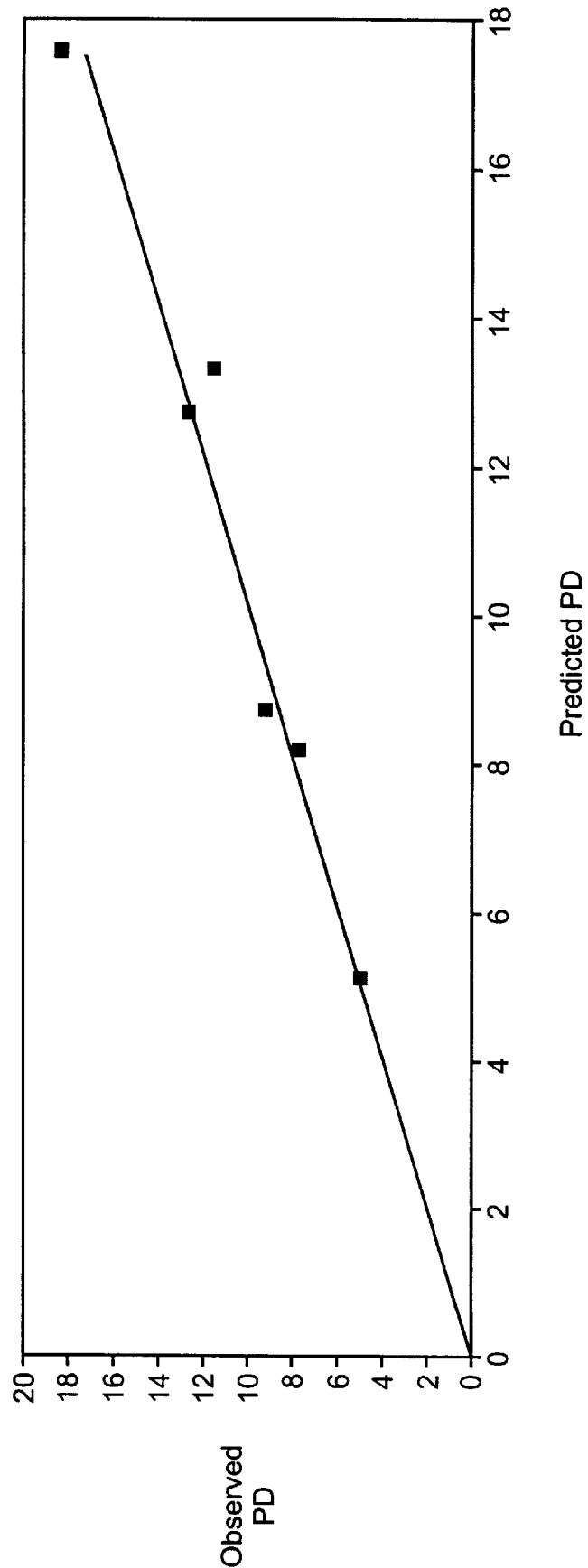
FIG. 7 Observed versus predicted flare response.
Figure 8:
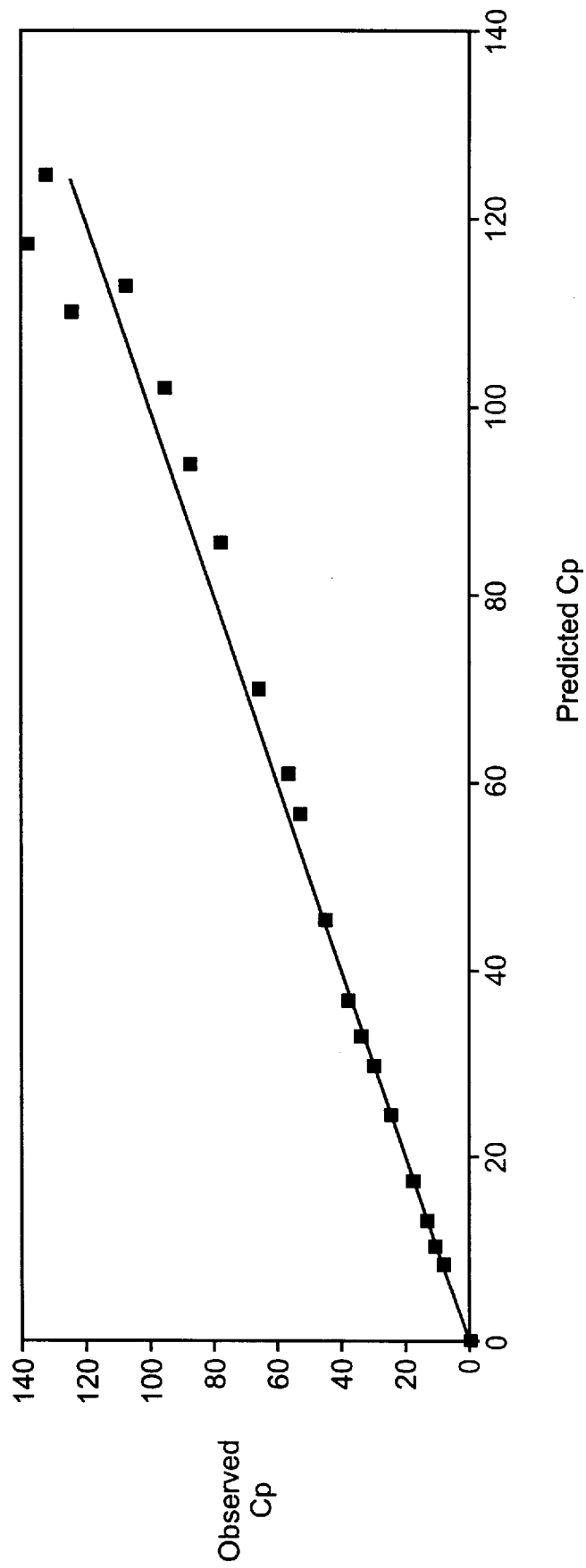
FIG. 8 Observed plasma concentration of acrivastine versus predicted plasma concentration based on model of FIG. 5, for peak saccade velocity response.
Figure 9:
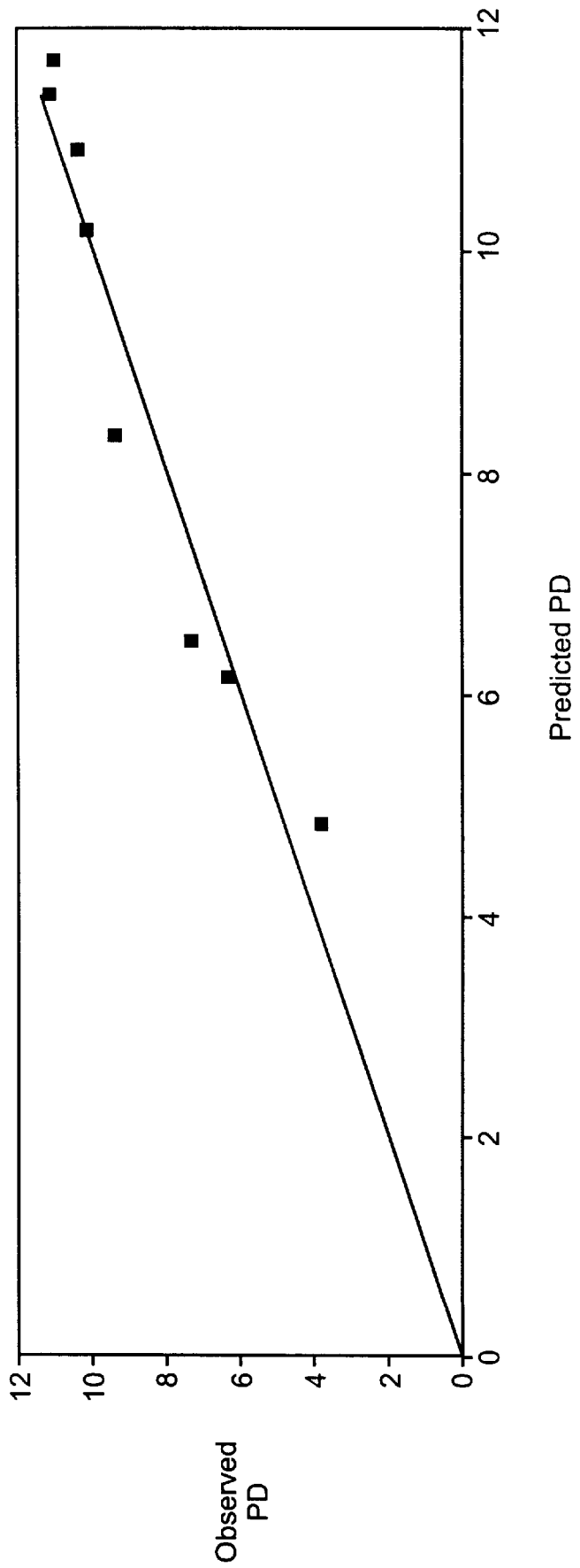
FIG. 9 Observed versus predicted peak saccade velocity response.
Figure 10:
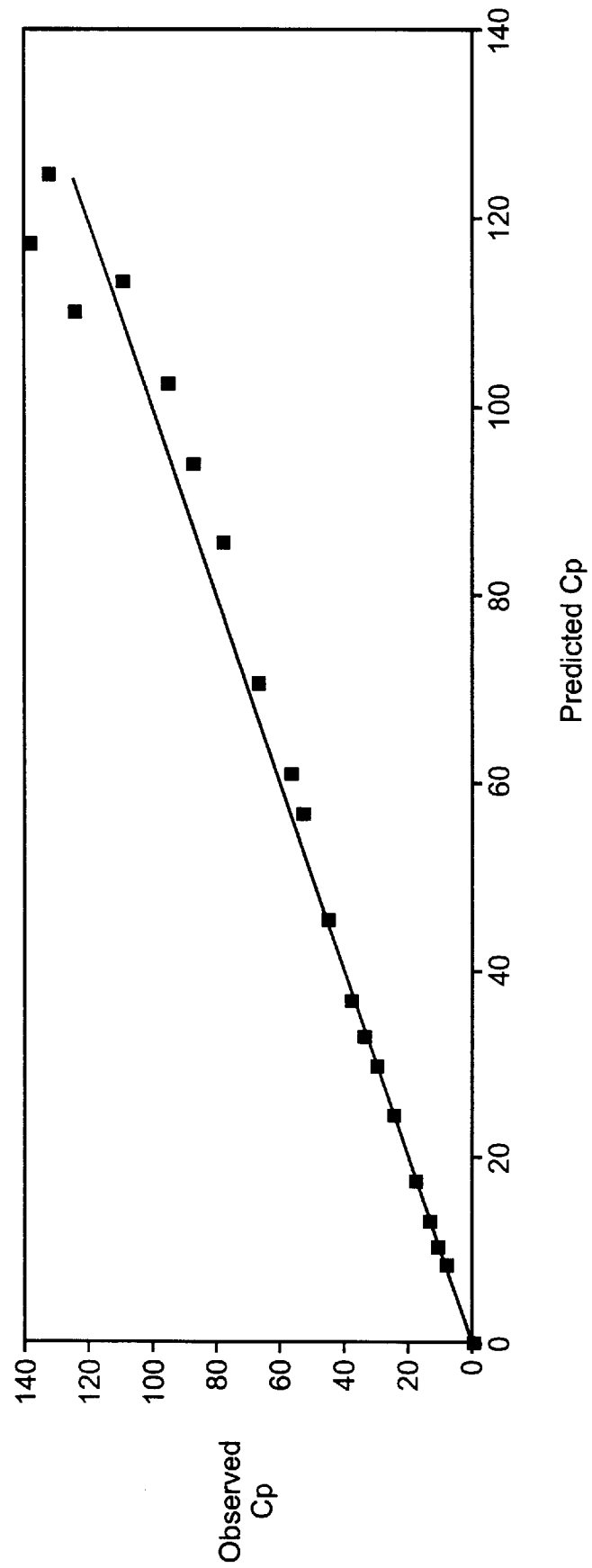
FIG. 10 Observed plasma concentration of acrivastine versus predicted plasma concentration based on model of FIG. 5, for sway response.
Figure 11:
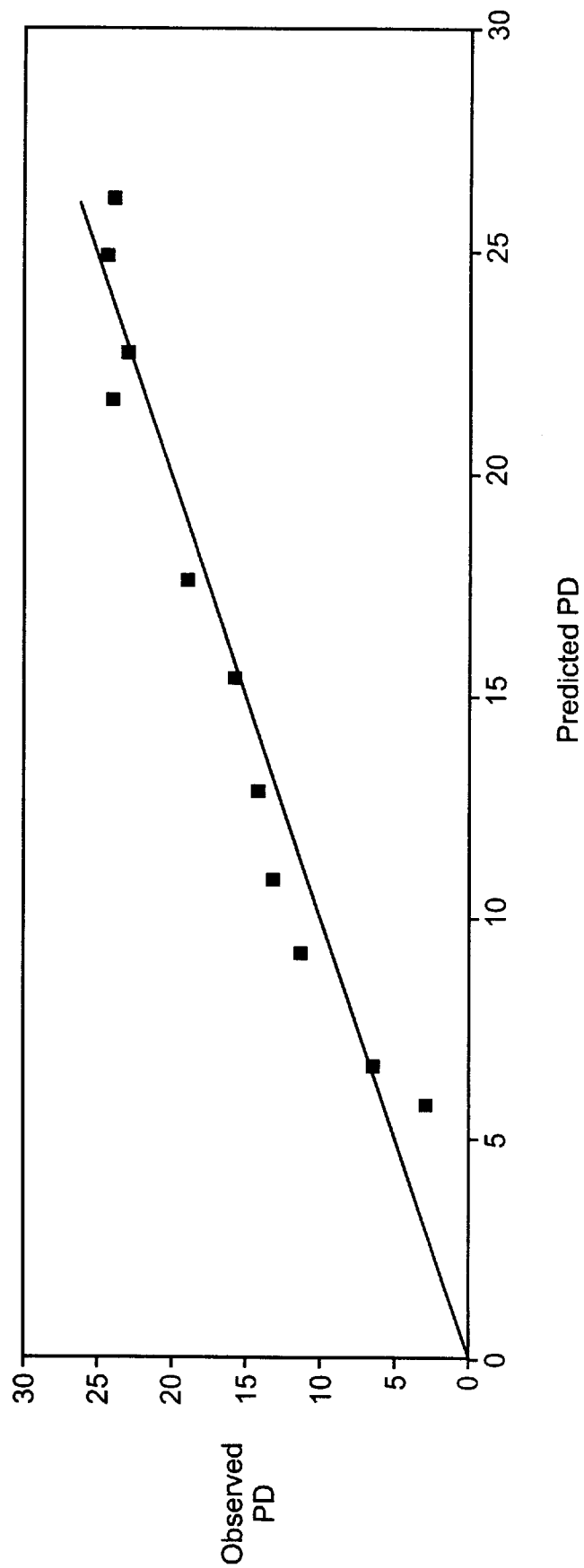
FIG. 11 Observed versus predicted sway response.

Pharmacokinetic estimates and pharmacodynamic parameter estimates were obtained independently for each pharmacodynamic response by simultaneously fitting drug plasma concentration data and pharmacodynamic data to a pharmacokinetic/pharmacodynamic model depicted in FIG. 5.

In this model, the effect compartment is linked to a standard two-compartment linear pharmacokinetic model. The rate constant $K_{12}$ describes a first-order absorption process from the gut to the central compartment and $K_0$ describes a zero-order absorption process. $K_{23}$ was set so that the effect compartment receives a negligible amount of drug. The first order rate constant $K_{30}$ and the equilibrium half-life $t_{1/2}K_{30}$ describe the delay in the equilibration of drug to the effect compartment.

The goodness of fit of the pharmacokinetic/pharmacodynamic model was assessed graphically by plotting predicted vs. observed plasma concentrations and predicted vs. observed pharmacodynamic responses. These plots are provided as FIGS. 6–11. The high level of correlation between observed and predicted plasma concentrations and pharmacodynamic responses seen in these figures indicates that the proposed model adequately describes the observed data.

The pharmacokinetic parameter estimates obtained for the three pharmacodynamic data sets are set forth in Table I.

TABLE I

|  | Flare | PSV | Sway |
| --- | --- | --- | --- |
| $K_{12}$, hr$^{-1}$ | 0.830 | 0.832 | 0.838 |
| $K_{20}$, hr$^{-1}$ | 0.6 | 0.6 | 0.6 |
| Vdc, L | 24.8 | 24.8 | 24.8 |
| $K_{24}$, hr$^{-1}$ | 0.179 | 0.180 | 0.180 |

TABLE I-continued

|  | Flare | PSV | Sway |
| --- | --- | --- | --- |
| $K_{42}$, hr$^{-1}$ | 0.176 | 0.178 | 0.189 |

The similarity of the pharmacokinetic parameter estimates obtained irrespective of the pharmacodynamic data which was being modeled indicates the minimal impact which pharmacodynamic data has on the pharmacokinetic parameter estimates. The terminal half-life was calculated to be about 5 hrs, however, approximately ⅔ of the plasma concentration time curve is governed by a much shorter 0.83 hr distribution half-life.

The pharmacodynamic estimates for Emax and EC50 for the three responses are shown below in Table II. Emax is the maximum pharmacodynamic response for each variable. EC50 is the concentration at the effect site at which one-half of the maximum response occurs. K30 is the rate constant that describes the delay in equilibrium of drug into the effect component.

TABLE II

|  | Emax units | EC50 ng/ml | K30 hr$^{-1}$ |
| --- | --- | --- | --- |
| Flare | 28.5% reduction in histamine-induced flare area | 29.7 | 0.965 |
| PSV | 28 degrees/sec. | 137 | 0.895 |
| Sway | 58 degrees/min. | 146 | 3.75 |

Figure 12:
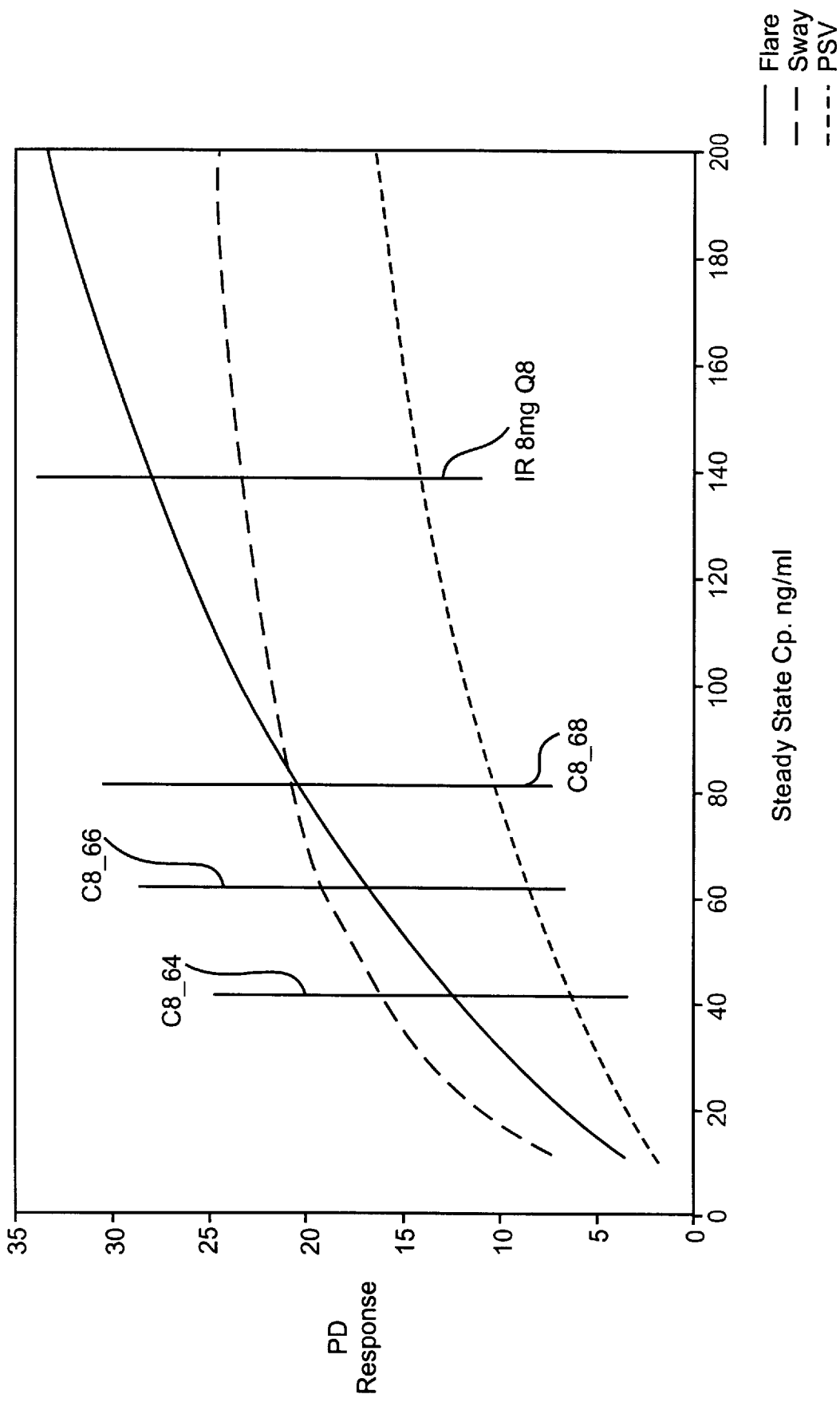
FIG. 12 Pharmacokinetic/pharmacodynamic relationships of flare, sway, and peak saccade velocity responses versus steady state plasma concentrations of acrivastine (ng/ml). Bars indicate achieved peak steady state plasma concentrations for four formulations as follows: $C8_{13}64$ corresponds to a 4 mg combination product with 0.5 mg immediate release (IR) component and 3.5 mg zero order component delivered over 6 hours and administered every 8 hours; $C8\_66$ corresponds to a 6 mg combination product with 0.75 mg IR component and 5.25 zero order component delivered over 6 hours and administered every 8 hours; $C8\_68$ corresponds to a 8 mg combination product with 1 mg IR component and 7 mg zero order component delivered over 6 hours and administered every 8 hours; and IR 8 mg Q8 corresponds to 8 mg immediate release acrivastine administered every 8 hours. Direct comparison can be made between the 8 mg IR product and the 8 mg combination product as indicated above. The 6 mg and 4 mg combination products can be used to see further reduction in the positive and negative pharmacodynamic effects.

These parameters can also be expressed in FIG. 12 which relates a given steady state acrivastine plasma concentration to pharmacodynamic (PD) response for the three PD responses evaluated. Inspection of this figure indicates that smaller changes in flare response than seen for PSV or sway would be expected for a given reduction in plasma concentration. This figure also shows the maximum plasma concentrations observed after administration of the current 8 mg immediate release (IR) tablet every 8 hours and following administration of 8, 6, and 4 mg controlled release products as described in Table III below (simulation of the impact of controlled rates of drug delivery on pharmacodynamic response).

While it would have been desirable to explore delivery of acrivastine at a very slow rate, allowing once or twice daily administration, the absorption characteristics of acrivastine preclude this. Acrivastine is thought to have site-specific absorption. A study in which pharmacokinetic profiles of acrivastine after oral and colonic administration were compared showed that acrivastine was poorly absorbed from the human colon. The relative bioavailability ($F_{rel}$) of acrivastine after colonic administration was 0.18±0.09 (Balasubramanian et al., supra). In another study the blood level profiles for a 12 mg acrivastine immediate release dose was compared to an experimental 12 mg controlled release dose. The blood level profile for the controlled release formulation showed an apparent truncation of absorption at 5–6 hours following drug administration and a significant decrease in bioavailability compared to the immediate release formulation (Jones et al, supra).

Given this problem, a maximum duration for drug delivery by a zero order process of 6 hours was selected. Since the elimination time for acrivastine is very short, the experiment included a 12.5% immediate release (IR) component to accelerate attainment of plateau concentrations. Due to uncertainty regarding plasma concentrations required for optimal antihistaminic effect, dosage forms containing 8, 6 and 4 mg prepared as set forth in Table III were evaluated:

TABLE III

| Total dose | IR component | Zero Order Dose | In Vivo Zero Order Rate (6 hr duration) |
|---|---|---|---|
| 8 mg | 1 mg | 7 mg | 1.17 mg/hr |
| 6 mg | 0.75 mg | 5.25 mg | 0.875 mg/hr |
| 4 mg | 0.5 mg | 3.5 mg | 0.583 mg/hr |

Figure 13:
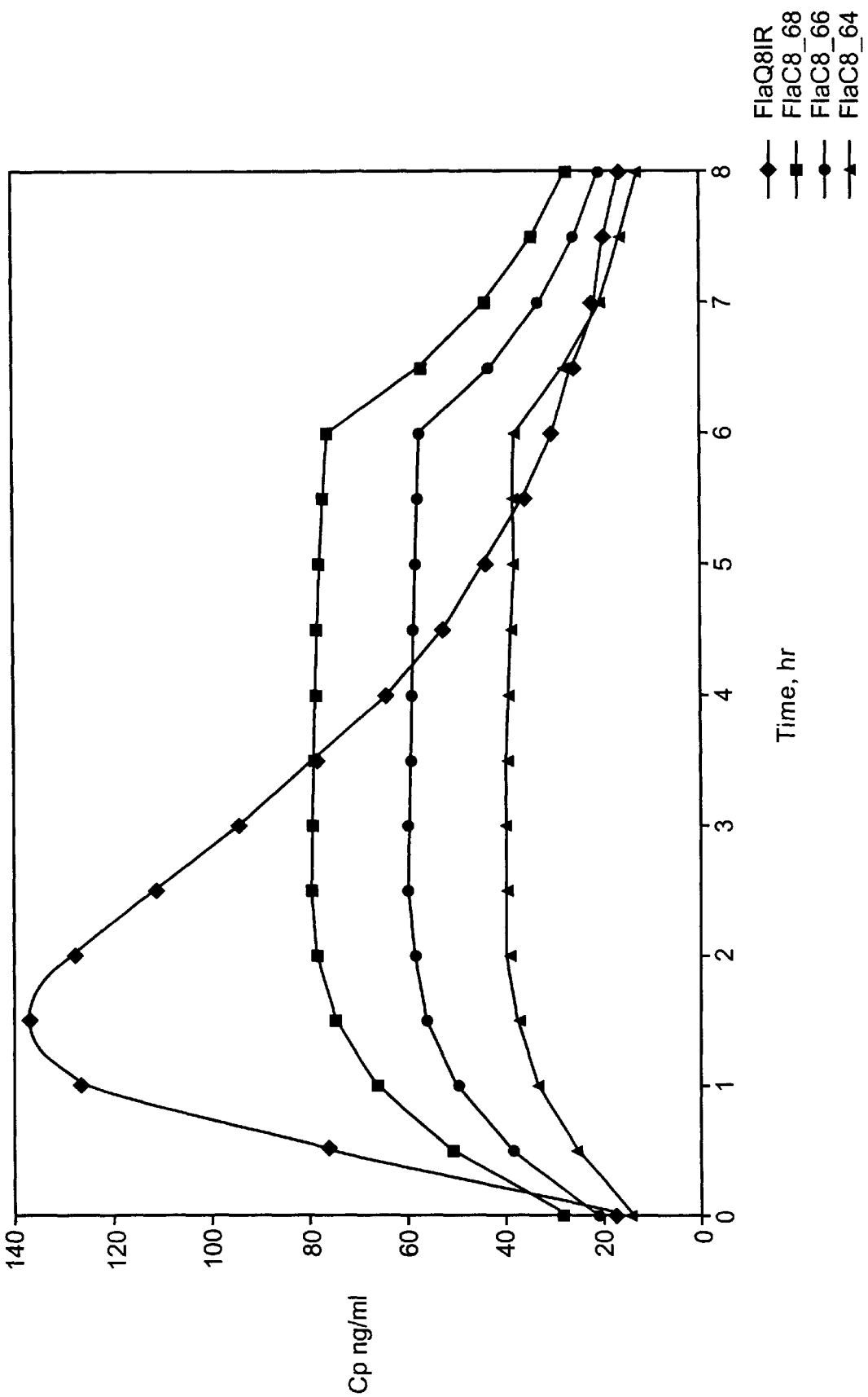
FIG. 13 Steady state plasma concentrations of acrivastine simulated following administration of IR 8 mg Q8 and controlled release $C8_{13}68$, $C8_{13}66$, and $C8_{13}64$ preparations, as derived from data relating to the flare response.
Figure 14:
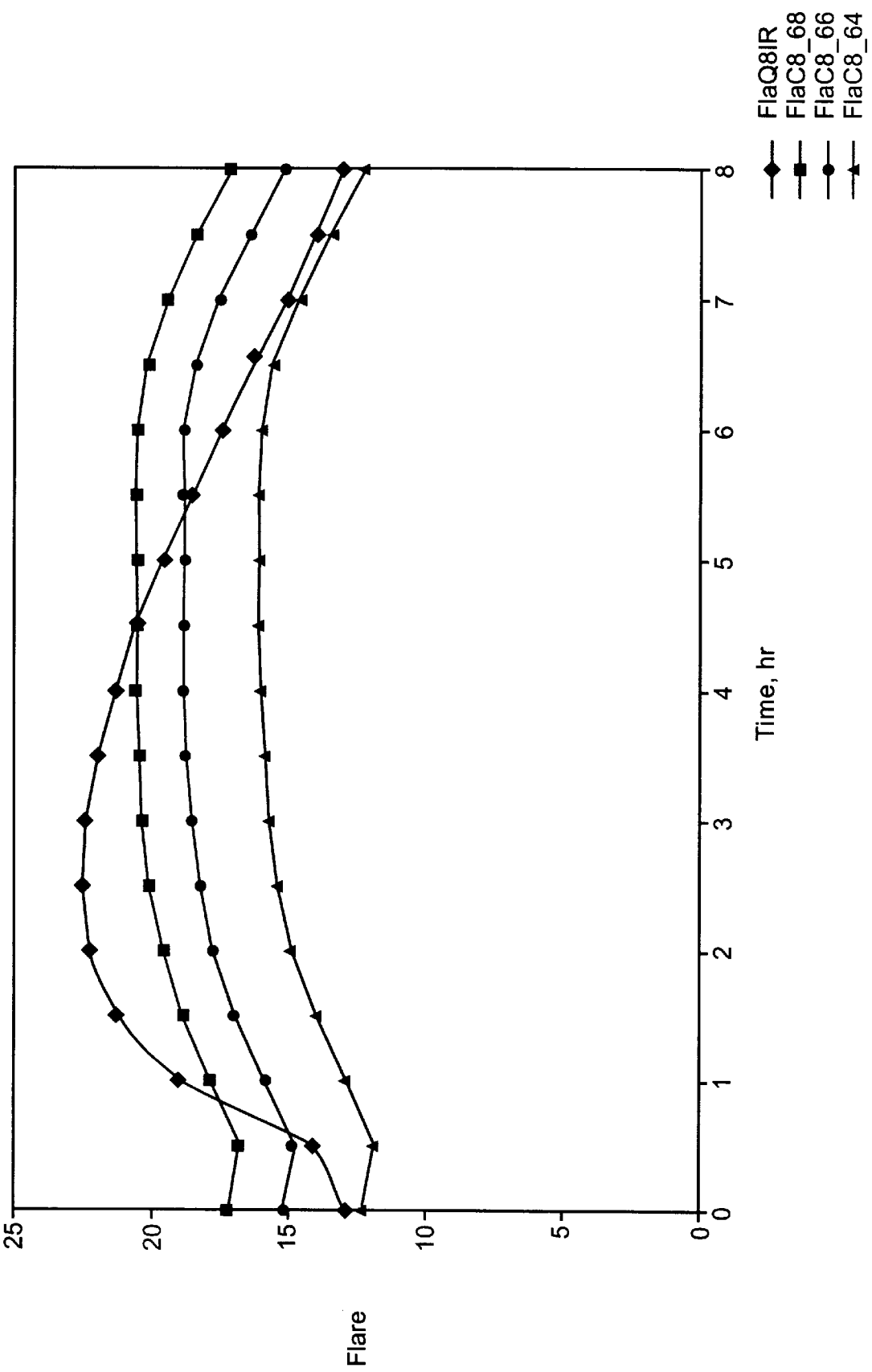
FIG. 14 Steady state pharmacodynamic flare responses for IR 8 mg Q8 and controlled release $C8_{13}68$, $C8_{13}66$, and $C8_{13}64$ formulations.
Figure 15:
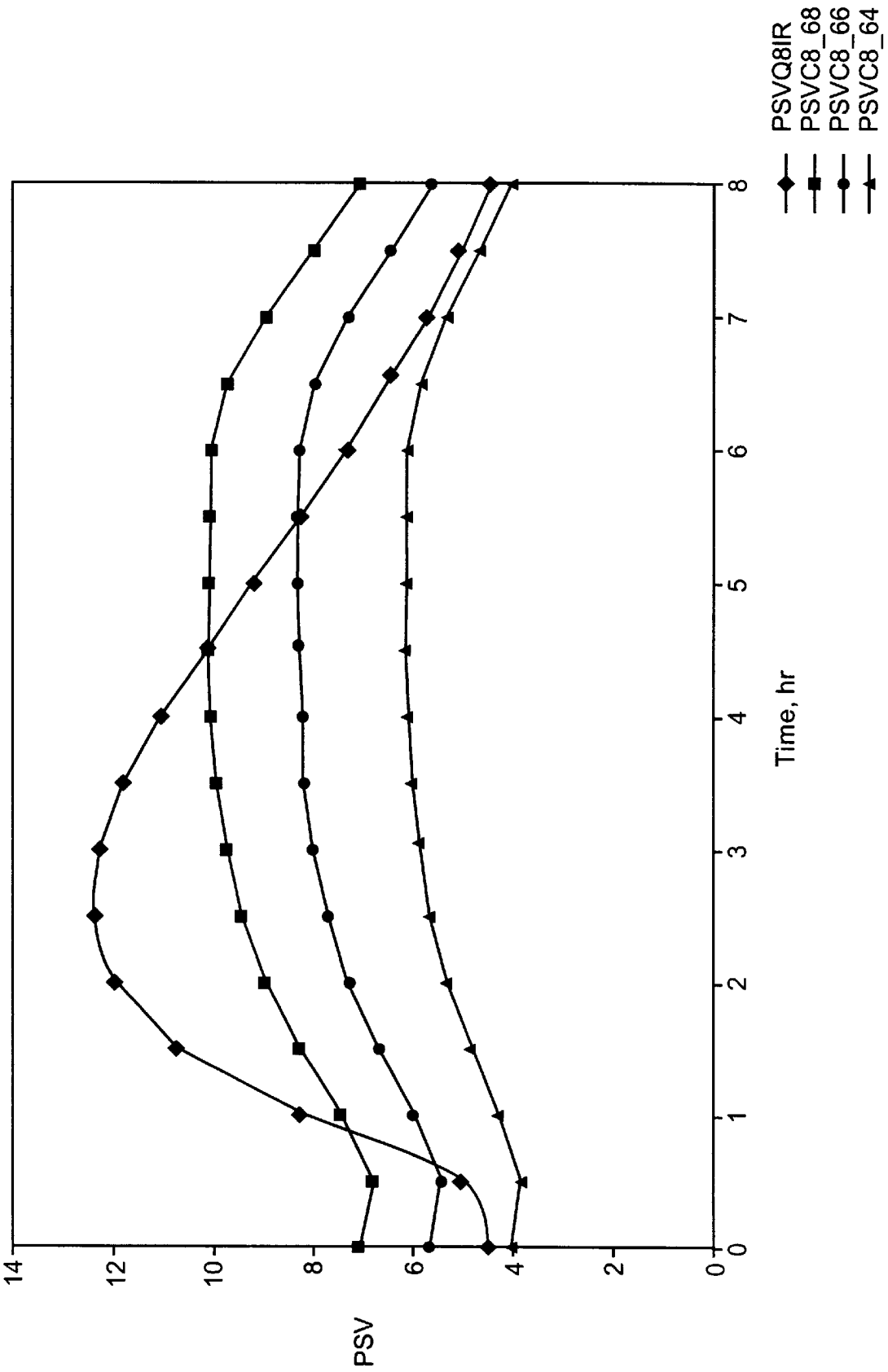
FIG. 15 Steady state pharmacodynamic peak saccade velocity responses for IR 8 mg Q8 and controlled release $C8_{13}68$, $C8_{13}66$, and $C8_{13}64$ formulations.
Figure 16:
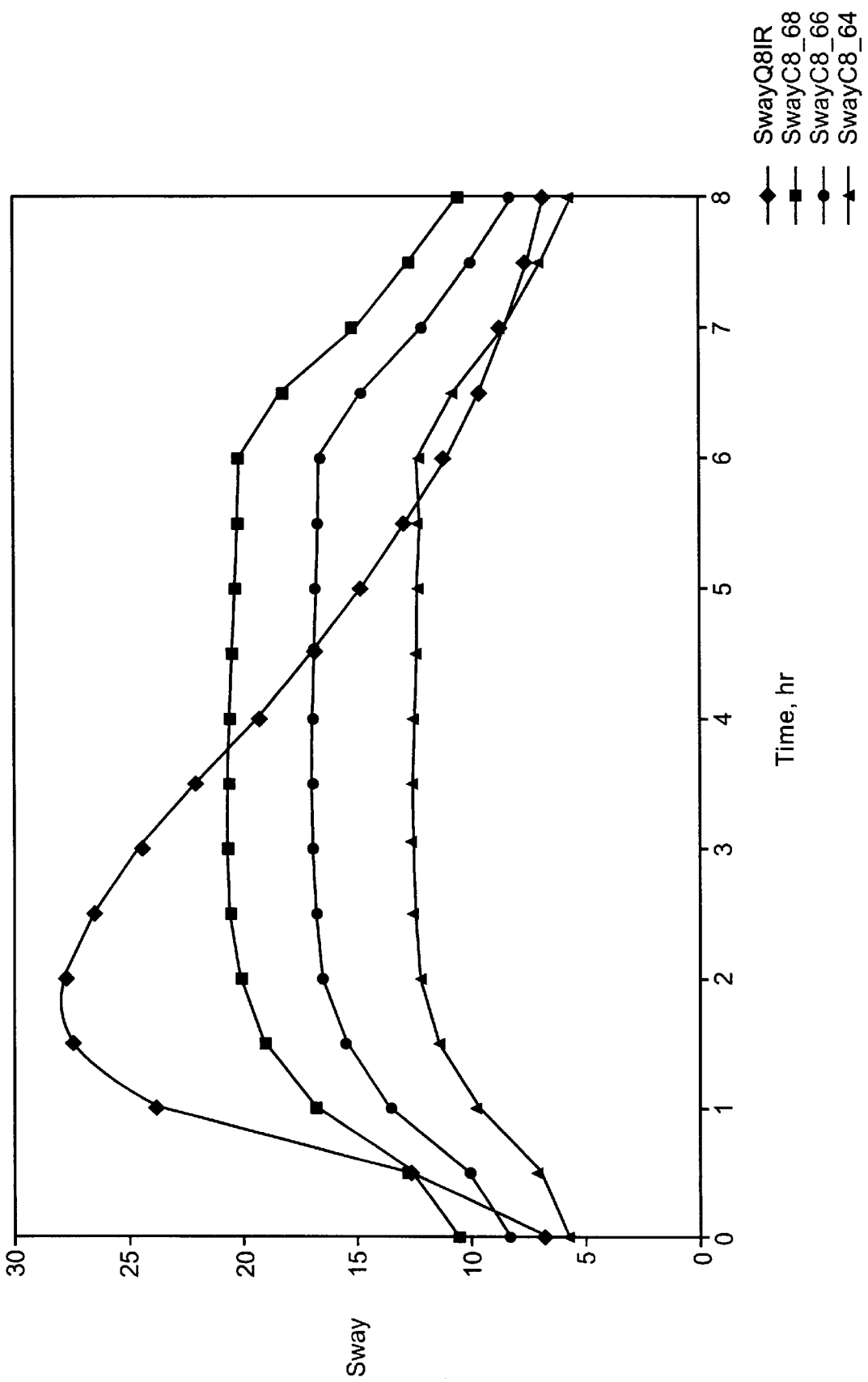
FIG. 16 Steady state pharmacodynamic sway responses for IR 8 mg Q8 and controlled release $C8_{13}68$, $C8_{13}66$ and $C8_{13}64$ formulations.

Steady state plasma acrivastine concentrations simulated following administration of an 8 mg IR product and the three controlled release products described above are presented in FIG. 13. These concentrations were virtually identical regardless of the parameter set used for simulations, thus only values derived from the flare data are presented. Steady state pharmacodynamic responses for these four formulations are depicted in FIGS. 14–16 for flare, sway, and PSV, respectively.

Table IV shows percent reduction in maximum response for the three pharmacodynamic parameters for the three controlled doses of 8 mg, 6 mg and 4 mg respectively, compared to that of 8 mg IR product.

TABLE IV

| % Decrease in Peak PD Effect (compared to 8 mg IR) | | | |
|---|---|---|---|
| | C_6 8 mg q8 h | C_6 6 mg q8 h | C_6 4 mg q8 h |
| flare | −8 | −16 | −28 |
| sway | −25 | −39 | −55 |
| psv | −18 | −33 | −50 |

KEY
Combn. 8 mg = C_68 mg q8 h.
Combn. 6 mg = C_66 mg q8 h.
Combn. 4 mg = C_64 mg q8 h.

The foregoing pharmacokinetic/pharmacodynamic analysis and resulting simulations indicate that the sedative effects of acrivastine can be reduced to a greater extent (about 2 to 3 fold) than the reduction in antihistaminic response by modifying and controlling the rate of drug delivery. Various publications are cited herein, the contents of which are hereby incorporated, by reference, in their entireties.

EXAMPLE II

Acrivastine In Vivo Sustained Release Determinations

Figure 17:
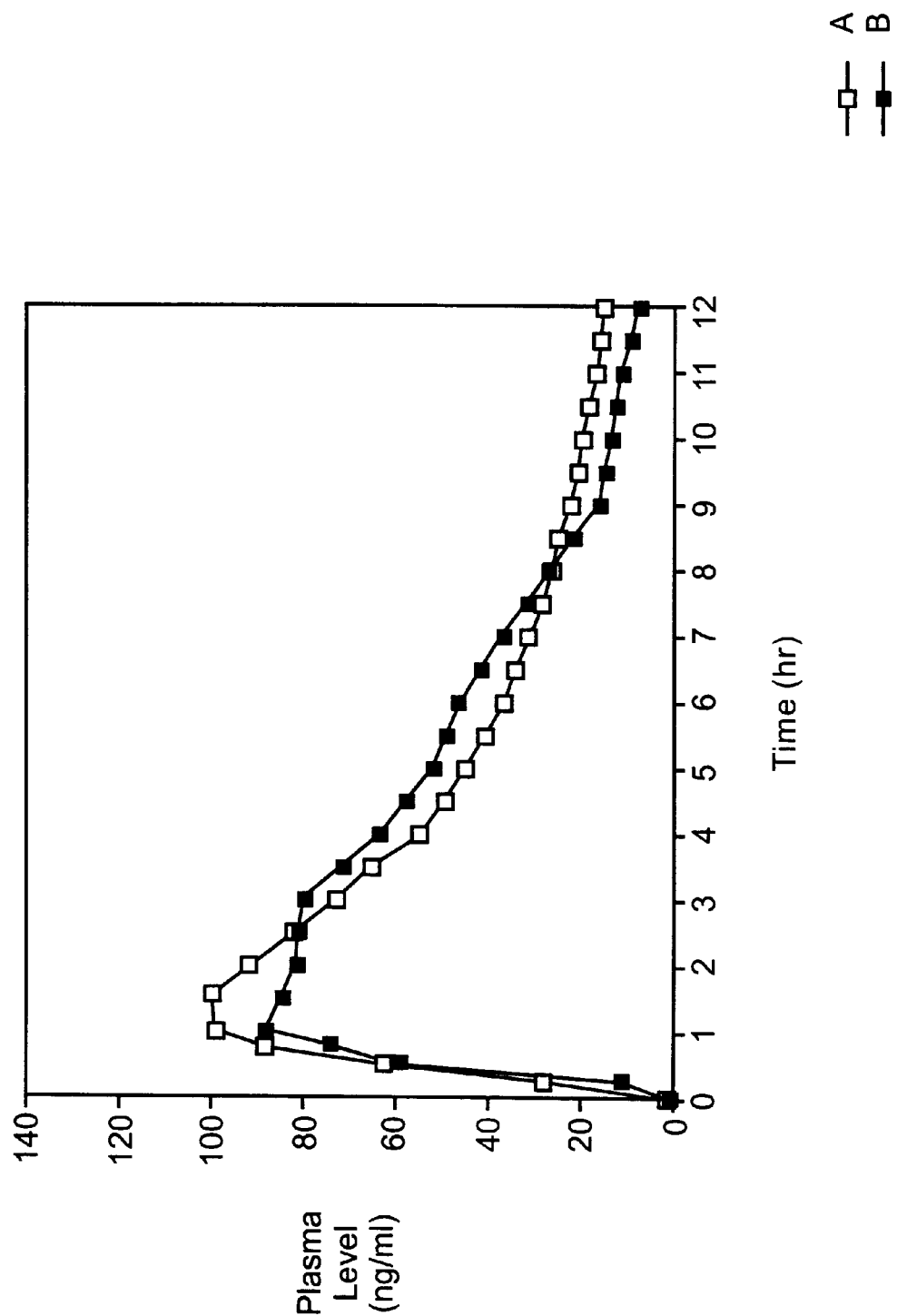
FIG. 17 A plot comparing the mathematically predicted concentrations of acrivastine (ng/ml) in the plasma over time for 8 mg controlled release acrivastine preparations. Data supplied by the present inventors (-□-) is compared with data provided in Jones et al., 104 INTERNATIONAL JOURNAL OF PHARMACEUTICS 253 (1994)(-■-). These plots were generated using the mathematical model of Jones et al.

From the pharmacokinetic parameters previously established for acrivastine and the desired in vivo steady-state plasma levels of these formulations, the necessary in vitro dissolution profiles of controlled release formulations were predicted, using the mathematical model of Jones et al. 104 INTERNATIONAL JOURNAL OF PHARMACEUTICS 253 (1994). These studies permit determination of the range of dissolution profiles giving rise to steady state plasma concentration plateaus at 60, 80 and 100 ng/ml of acrivastine.
Development of Acrivastine In Vivo Simulations:

The method and equations used to generate in vivo plasma concentration curves from in vitro dissolution profiles are described in Jones et al. (1994). A comparison of the results obtained using the in vitro dissolution data for an 8 mg dosage form provided by Jones et al. (1994) and the in vitro dissolution data generated for an 8 mg dosage form of the present invention are depicted in FIG. 17. The two predicted curves are similar.

Figure 18:
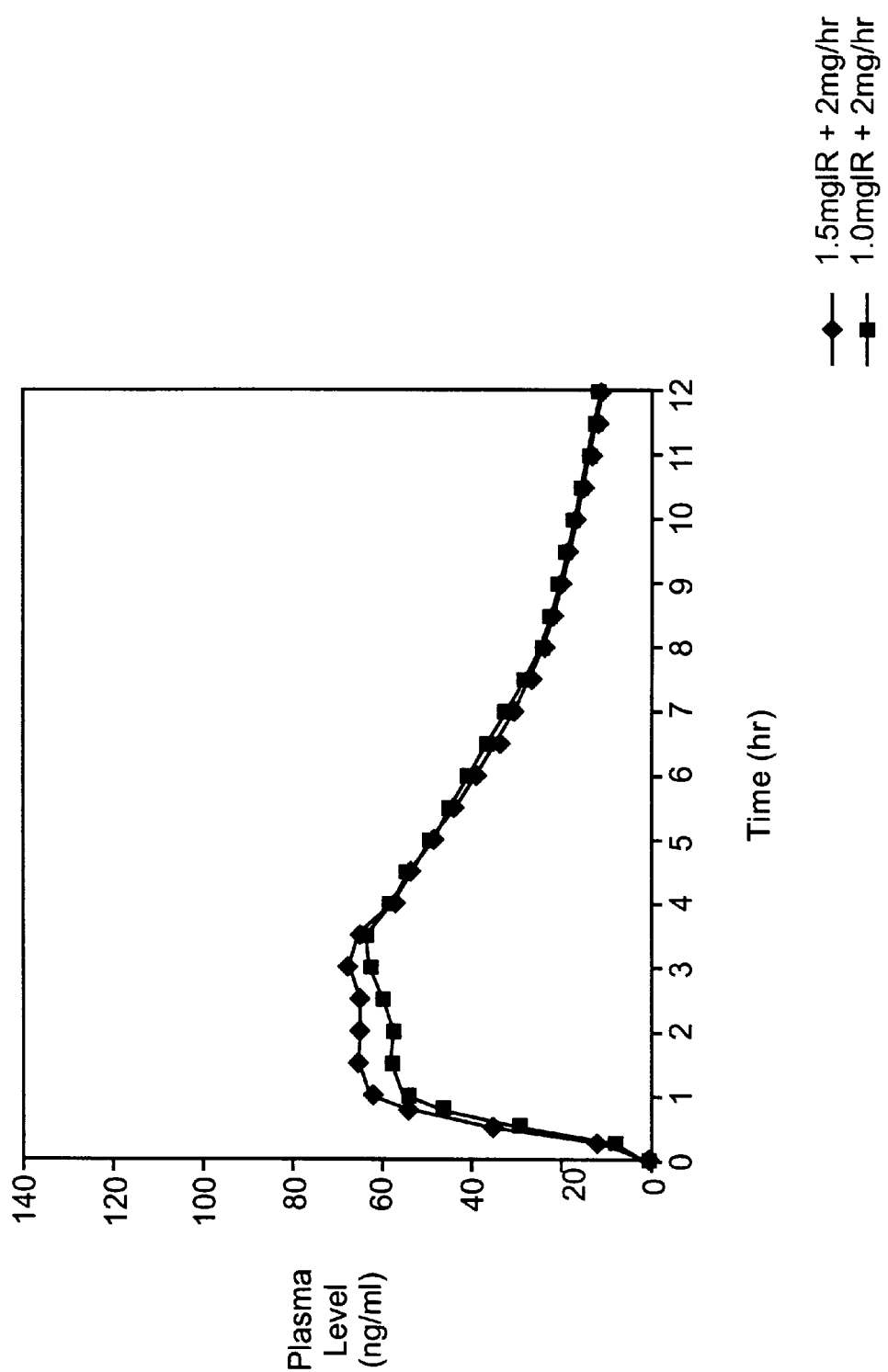
FIG. 18. A plot comparing the mathematically predicted concentrations of acrivastine (ng/ml) in the plasma over time for two 8 mg controlled release acrivastine preparations when the targeted plasma level is 60 ng/ml. Two different formulations, with the indicated immediate release (IR) and release rates (in mg/hr) could be made to fit the in vivo 60 ng/ml plasma level over an extended time. The first formulation had an immediate release of 1.5 mg with a release rate of 2 mg/hr (-♦-); the second formulation had an immediate release of 1.0 mg with a release rate of 2 mg/hr (-■-). These plots were generated using the mathematical model of Jones et al., 104 INTERNATIONAL JOURNAL OF PHARMACEUTICS 253 (1994).
Figure 19:
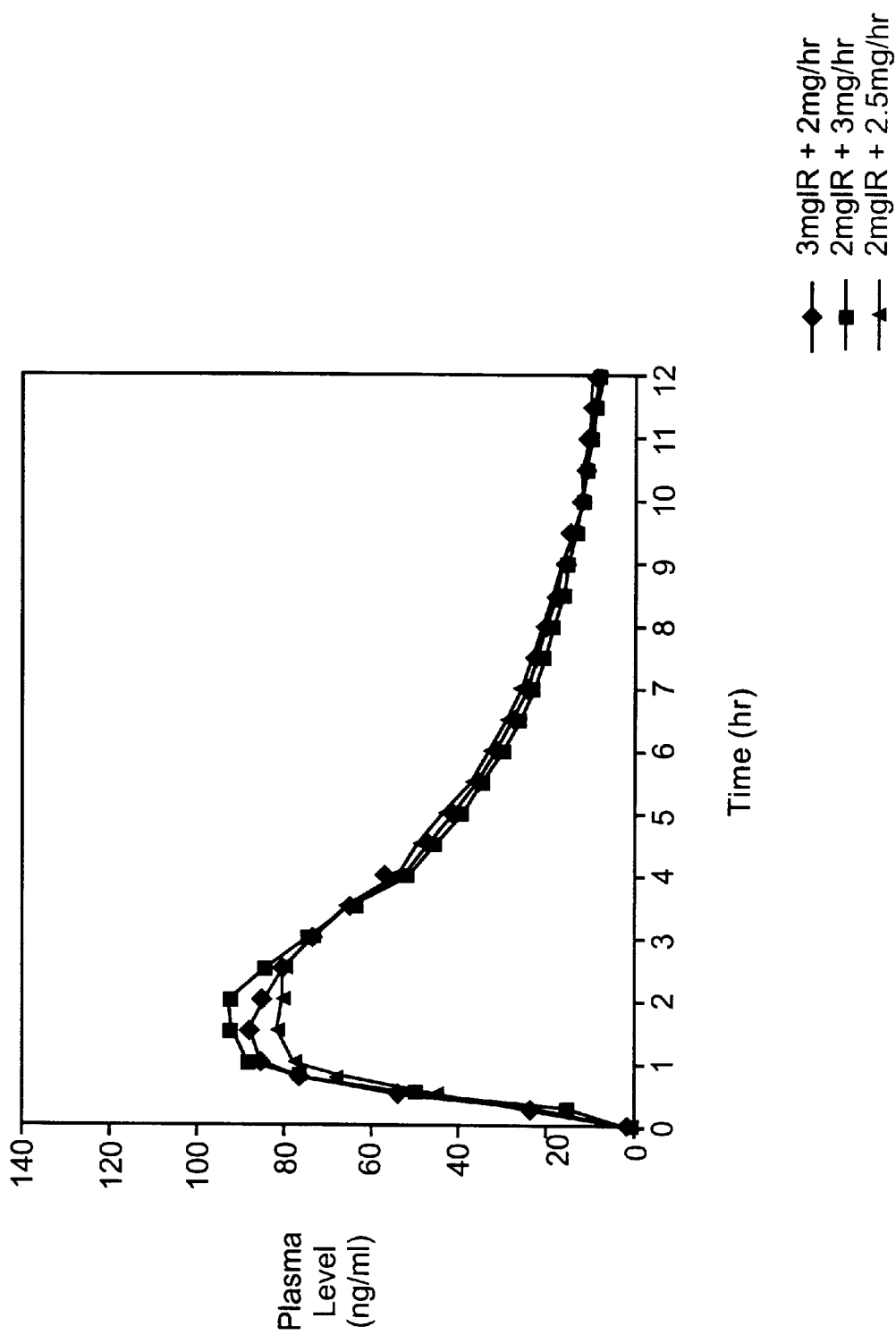
FIG. 19. A plot comparing the mathematically predicted concentrations of acrivastine (ng/ml) in the plasma over time for three 8 mg controlled release acrivastine preparations when the targeted plasma level is 80 ng/ml. Three different formulations, with the indicated immediate release (IR) and release rates (in mg/hr) could be made to fit the in vivo 80 ng/ml plasma level over an extended time. The first formulation had an immediate release of 3 mg with a release rate of 2 mg/hr (-★-); the second formulation had an immediate release of 2 mg with a release rate of 3 mg/hr (-■-); the third formulation had an immediate release of 2 mg with a release rate of 2.5 mg/hr (-▲-). These plots were generated using the mathematical model of Jones et al., 104 INTERNATIONAL JOURNAL OF PHARMACEUTICS 253 (1994).
Figure 20:
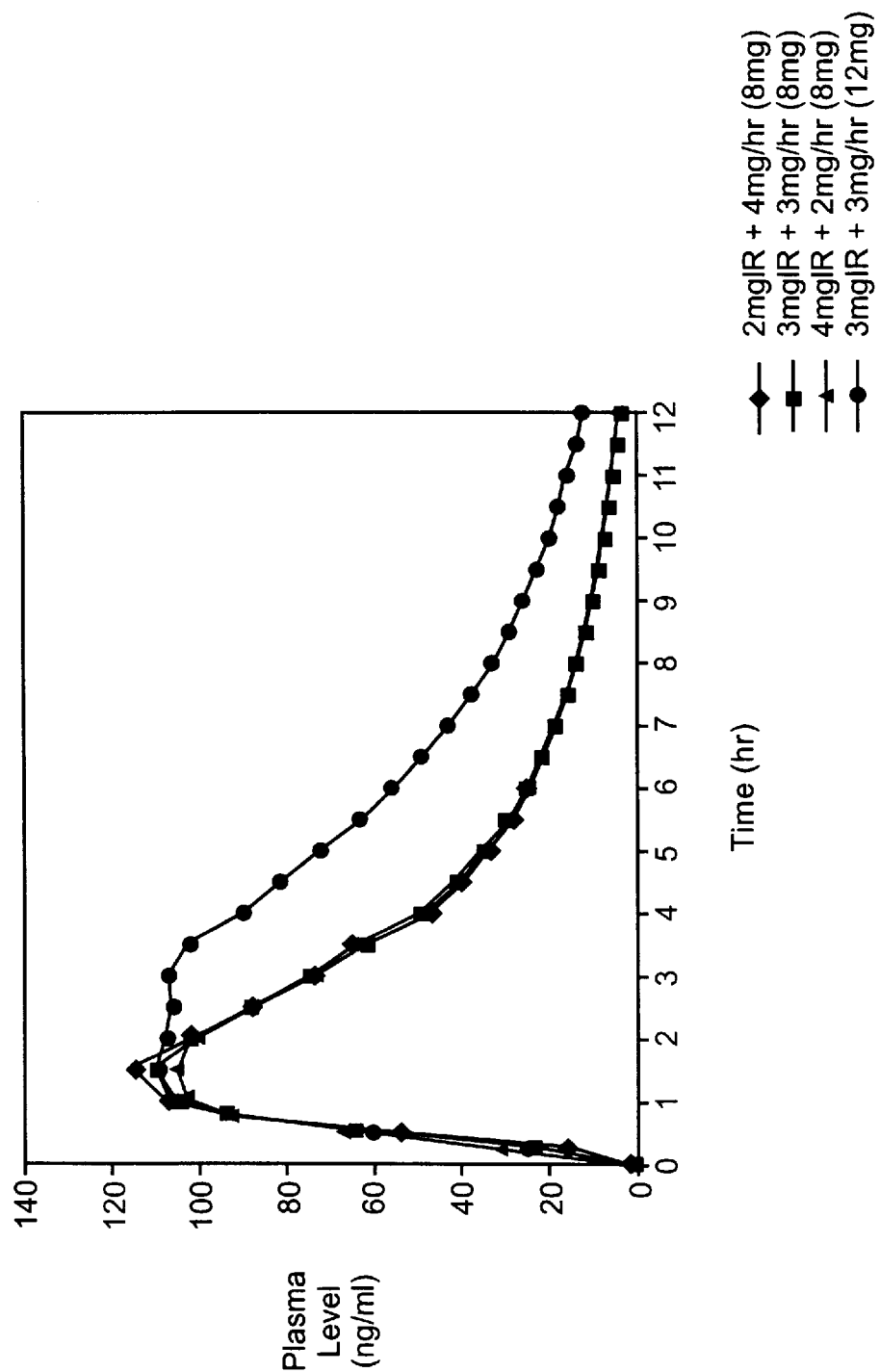
FIG. 20 A plot comparing the mathematically predicted concentrations of acrivastine (ng/ml) in the plasma over time for three 8 mg and one 12 mg controlled release acrivastine preparation when the targeted plasma level is 100 ng/ml. The 12 mg controlled release formulations, with an immediate release (IR) of 3 mg and a release rate of 3 mg/hr could be made to fit the in vivo 100 ng/ml plasma level over an extended time (-●-). The three 8 mg formulations did not fit the 100 ng/ml plasma level as well as the 12 mg formulation over time. Those three 8 mg formulations had: (1) an immediate release of 2 mg with a release rate of 4 mg/hr (-★-); (2) had an immediate release of 3 mg with a release rate of 3 mg/hr (-■-); and (3) an immediate release of 4 mg with a release rate of 2 mg/hr (-▲-). These plots were generated using the mathematical model of Jones et al., 104 INTERNATIONAL JOURNAL OF PHARMACEUTICS 253 (1994).

FIGS. 18–20 provide simulated acrivastine plasma concentration plateaus at around 60, 80 and 100 ng/ml, respectively. A plateau level of 100 ng/ml could only be generated with a 12 mg dose.

Figure 21:
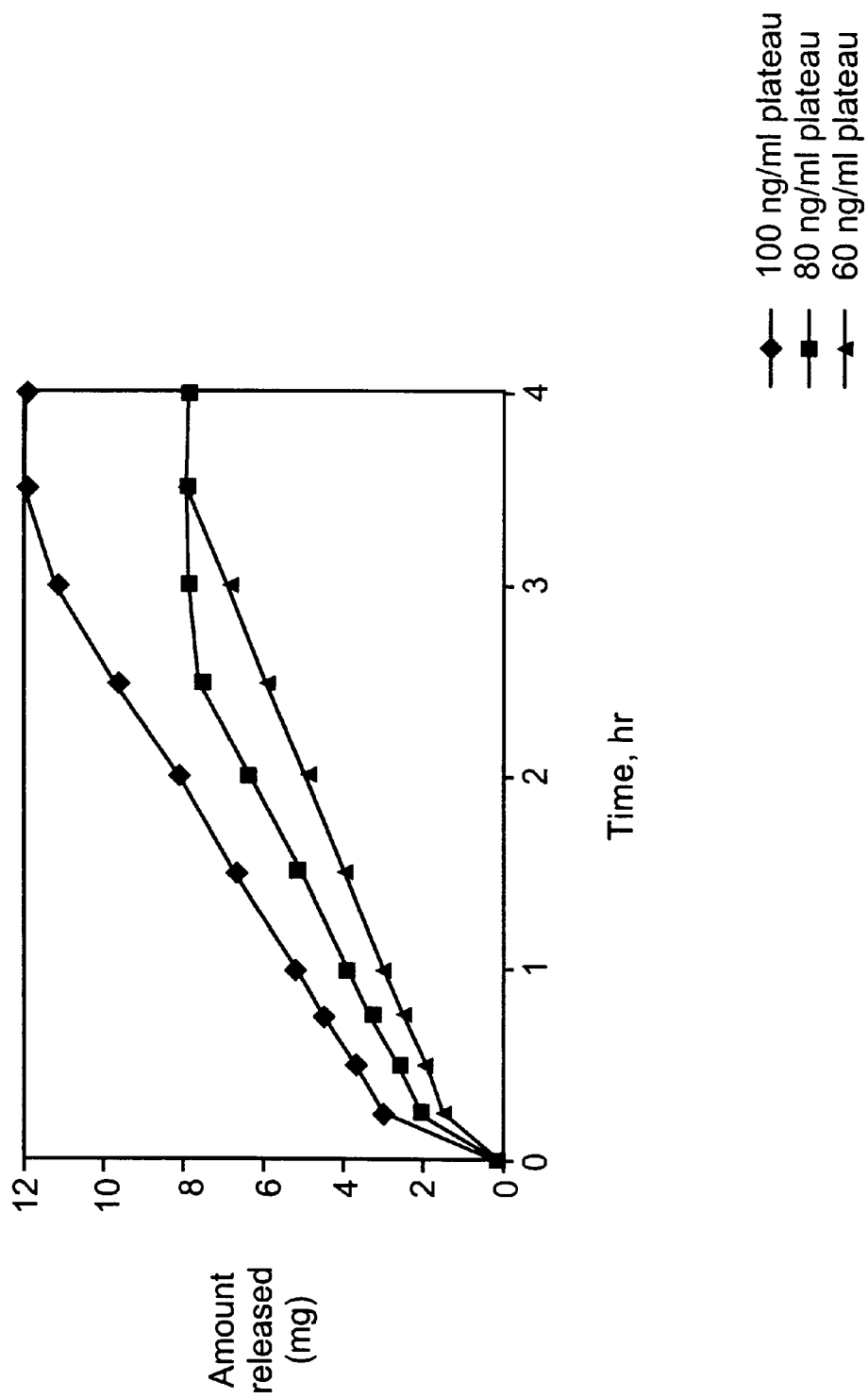
FIG. 21 A plot of the amount of drug release over time for three different plasma concentration plateaus.

Two to three simulations for the different plasma concentration plateaus are provided for each of FIGS. 18–20, corresponding to two to three different tablet preparations and their corresponding dissolution patterns. Two points from the in vitro dissolution pattern of these tablet preparations, corresponding to an immediate release (IR) and a release over time (in mg/hr), are noted on the appropriate figure and provided in Table V. FIG. 21 illustrates some of the in vitro release profiles of tablets used for the in vivo simulations.

TABLE V

| | mg Acrivastine Released Immediately (IR) and Over Time (mg/hr) | | |
|---|---|---|---|
| Dosage | Plasma level 60 ng/ml | Plasma level 80 ng/ml | Plasma level 100 mg/ml |
| 8 mg | 1.5 mg IR + 2 mg/hr | 3 mg IR + 2 mg/hr | 2 mg IR + 4 mg/hr |
| 8 mg | 1.0 mg IR + 2 mg/hr | 2 mg IR + 3 mg/hr | 3 mg IR + 3 mg/hr |
| 8 mg | | 2 mg IR + 2.5 mg/hr | 4 mg IR + 2 mg/hr |
| 12 mg | | | 3 mg IR + 3 mg/hr |

The release profiles of acrivastine tablets needed to obtain steady-state plasma concentration plateaus at 60, 80 and 100 ng/ml were determined. Plateau levels of 60 and 80 ng/ml could be generated with acrivastine doses of 8 mg. However, a plateau level of 100 ng/ml could be generated only with a 12 mg dose.

EXAMPLE III

Preparation of an Acrivastine Sustained Release Formulation

Example A

Acrivastine (14 g), cross-linked amylose (110.25 g) (available from Labopharm, Inc., Quebec, Canada), lactose (45.5 g) and pancreatine (1.75 g) were mixed vigorously for 3 min. Sodium benzoate (3.5 g) was added and the powder mixture was mixed for another 1 min. This powder blend was tableted to produce 100 mg tablets with a hardness of 95–120 N, a diameter of ¼ inches and a thickness of 3.10–3.30 mm. Each tablet contained 8 mg of acrivastine.
Examples B and C Two additional tablets were prepared. Both contained the same amounts of acrivastine, pancreatine, and sodium benzoate. Example B contained 124.25 grams of cross-linked amylose and 31.50 grams of lactose. Example C contained 98 grams of cross-linked amylose and 57.75 grams of lactose. The tablets were prepared in the same manner as Example A.
Comparative Example Acrivastine (8.00 Grams) and microcrystalline cellulose (90.00 grams) were mixed vigorously for three minutes. Sodium benzoate (2.0 grams) was added and the powder was mixed for an additional minute. The tablets were prepared in the same manner as Examples A–C. Each tablet contained 8 mg of acrivastine.

What is claimed is:

1. A method of producing an antihistaminic therapeutic effect while reducing a neurological side effect which comprises administering a controlled release formulation comprising a therapeutically effective amount of acrivastine to produce a peak acrivastine plasma concentration of less than about 100 ng/ml and a more uniform acrivastine plasma concentration than the acrivastine plasma concentration provided by the same dosage of an immediate release acrivastine formulation so that the neurological side effect is reduced while maintaining the antihistaminic therapeutic effect.

2. The method of claim 1, wherein said more uniform acrivastine plasma concentration is about 20 to about 90 ng/ml.

3. The method of claim 1, wherein said more uniform acrivastine plasma concentration is about 40 to about 80 ng/ml.

4. The method of claim 1, wherein said peak acrivastine plasma concentration is about 90 ng/ml.

5. The method of claim 1 wherein said therapeutically effective amount of acrivastine is about 6 mg to about 12 mg acrivastine.

6. The method of claim 1 wherein said therapeutically effective amount of acrivastine is about 8 mg acrivastine.

7. The method of claim 1, which further comprises achieving said peak acrivastine plasma concentration within about one hour of administering said formulation.

8. The method of claim 1, which further comprises reducing a neurological side effect by about 18 to about 55 percent relative to a neurological side effect obtained by an administration of an immediate release acrivastine formulation of the same dosage.

9. The method of claim 8 wherein said neurological side effect is sedation.

10. The method of claim 9 wherein said neurological side effect is measured by peak saccade velocity or body sway.

11. In a method of administering a pharmaceutical compound to a mammal, wherein the compound produces at least two physiological effects, the improved method comprising:

administering the compound in a controlled release formulation at the same therapeutic dose and dosing interval of an immediate release formulation to optimize a first physiological effect over a second physiological effect wherein said pharmaceutical compound comprises acrivastine.

12. The method according to claim 11, wherein the first physiological effect is an antihistaminic effect.

13. The method according to claim 11, wherein the second physiological effect is a neurological side effect.

14. A method of producing an antihistaminic therapeutic effect which comprises administering a controlled release formulation comprising a therapeutically effective amount of acrivastine to produce a peak acrivastine plasma concentration which is no more than 70% of the peak acrivastine plasma concentration provided by the same dosage of an immediate release acrivastine formulation.

15. The method of claim 14 wherein said therapeutically effective amount of acrivastine is about 6 mg to about 12 mg acrivastine.

16. The method of claim 14 wherein said therapeutically effective amount of acrivastine is about 8 mg acrivastine.

17. The method of claim 14, which further comprises achieving said peak acrivastine plasma concentration within about one hour of administering said formulation.

18. The method of claim 14, which further comprises reducing a neurological side effect by about 18 to about 55 percent relative to a neurological side effect obtained by an administration of an immediate release acrivastine formulation of the same dosage.

19. The method of claim 18, wherein said neurological side effect is sedation.

20. The method of claim 18, wherein said neurological side effect is measured by peak saccade velocity or body sway.

21. A controlled release acrivastine formulation comprising a therapeutically effective dosage of acrivastine which, when administered to a mammal, provides a peak plasma concentration of acrivastine of less than about 100 ng/ml and a more uniform acrivastine plasma concentration than the acrivastine plasma concentration provided by an immediate release formulation of acrivastine of the same dosage so as to reduce neurological side effects associated with the immediate release formulations.

22. The controlled release acrivastine formulation of claim 21 wherein said more uniform acrivastine plasma concentration is about 20 to about 90 ng/ml.

23. The controlled release acrivastine formulation of claim 21, wherein said more uniform acrivastine plasma concentration is about 40 to about 80 ng/ml.

24. The controlled release acrivastine formulation of claim 21, which further achieves said peak plasma concentration within about one hour of administration.

25. The controlled release acrivastine formulation of claim 21, which provides an neurological side effect that is about 20 to about 80 percent less than the neurological side effect provided by an immediate release acrivastine formulation of the same dosage.

26. The controlled release acrivastine formulation of claim 21 wherein said neurological side effect is sedation.

27. The controlled release acrivastine formulation of claim 21 wherein said neurological side effect is measured by peak saccade velocity or body sway.

28. The controlled release acrivastine formulation of claim 21, which further comprises cross-linked amylose.

29. The controlled release acrivastine formulation of claim 21 wherein said therapeutically effective amount of acrivastine is about 6 to about 12 mg acrivastine.

30. The controlled release acrivastine formulation of claim 21 wherein said therapeutically effective amount of acrivastine is about 8 mg acrivastine.

31. The controlled release acrivastine formulation of claim 21, wherein one part of acrivastine is mixed with five to twelve parts of cross-linked amylose.

32. The controlled release acrivastine formulation of claim 21 which further comprises administering said formulation at the same dosing frequency as an acrivastine immediate release formulation of the same dosage.

33. The controlled release acrivastine formulation of claim 21, which further comprises an antitussive, antihistamine, decongestant, non-steroid anti-inflammatory drug, alkaloid painkiller, anti-ulcer medication, $H_1$-antagonist, $H_2$-antagonist or stimulant, with the proviso that said decongestant is not (+)-pseudoephedrine.

34. A controlled release acrivastine formulation comprising a therapeutically effective amount of acrivastine which, when administered to a mammal, provides a peak plasma concentration of acrivastine which is no more than about 70% of the peak acrivastine plasma concentration provided by an immediate release formulation of acrivastine of the same dosage so as to reduce neurological side effects associated with the immediate release formulation.

35. The controlled release acrivastine formulation of claim 34, which further achieves said peak plasma concentration within about one hour of administration.

36. The controlled release acrivastine formulation of claim 34, which provides a neurological side effect that is about 20 to about 80 percent less than the neurological side effect provided by an immediate release acrivastine formulation of the same dosage.

37. The controlled release acrivastine formulation of claim 34 wherein said neurological side effect is sedation.

38. The controlled release acrivastine formulation of claim 34 wherein said neurological side effect is measured by peak saccade velocity or body sway.

39. The controlled release acrivastine formulation of claim 34 wherein said therapeutically effective amount of acrivastine is about 6 to about 12 mg acrivastine.

40. The controlled release acrivastine formulation of claim 34 wherein said therapeutically effective amount of acrivastine is about 8 mg acrivastine.

41. The controlled release acrivastine formulation of claim 34, which further comprises cross-linked amylose.

42. The controlled release acrivastine formulation of claim 34, wherein one part of acrivastine is mixed with five to twelve parts of cross-linked amylose.

43. The controlled release acrivastine formulation of claim 34 which further comprises administering said formulation at the same dosing frequency as an acrivastine immediate release formulation of the same dosage.

44. The controlled release acrivastine formulation of claim 34, which further comprises an antitussive, antihistamine, decongestant, non-steroid anti-inflammatory drug, alkaloid painkiller, anti-ulcer medication, $H_1$-antagonist, $H_2$-antagonist or stimulant, with the proviso that said decongestant is not (+)-pseudoephedrine.

45. In a method of administering a pharmaceutical compound to a mammal using an immediate release formulation at a known dosage amount and frequency that produces a pharmacokinetic profile with a known area under the curve, the improvement comprising administering the pharmaceutical compound at the same dosage amount and frequency using a sustained release formulation to produce a different pharmacokinetic profile wherein said pharmaceutical compound comprises acrivastine.

46. The method according to claim 45, wherein the known pharmacokinetic profile produces an adverse side effect and the modified pharmacokinetic profile reduces the adverse side effect.

\* \* \* \* \*